(12) United States Patent
Chan et al.

(10) Patent No.: US 9,744,318 B2
(45) Date of Patent: Aug. 29, 2017

(54) AEROSOLIZATION APPARATUS FOR INHALATION PROFILE-INDEPENDENT DRUG DELIVERY

(71) Applicants: Leo Chan, Fremont, CA (US); Keith Try Ung, Belmont, CA (US); Jeffry G. Weers, Belmont, CA (US)

(72) Inventors: Leo Chan, Fremont, CA (US); Keith Try Ung, Belmont, CA (US); Jeffry G. Weers, Belmont, CA (US)

(73) Assignee: Novartis AG, Basel (CH)

( * ) Notice: Subject to any disclaimer, the term of this patent is extended or adjusted under 35 U.S.C. 154(b) by 626 days.

(21) Appl. No.: 14/364,478

(22) PCT Filed: Dec. 14, 2012

(86) PCT No.: PCT/US2012/069938
§ 371 (c)(1),
(2) Date: Jun. 11, 2014

(87) PCT Pub. No.: WO2013/090841
PCT Pub. Date: Jun. 20, 2013

(65) Prior Publication Data
US 2014/0318539 A1    Oct. 30, 2014

Related U.S. Application Data

(60) Provisional application No. 61/576,735, filed on Dec. 16, 2011, provisional application No. 61/576,768, filed on Dec. 16, 2011.

(51) Int. Cl.
*A61M 15/00* (2006.01)
*A61K 31/66* (2006.01)
*A61M 11/00* (2006.01)

(52) U.S. Cl.
CPC ......... *A61M 15/0035* (2014.02); *A61K 31/66* (2013.01); *A61M 11/001* (2014.02);
(Continued)

(58) Field of Classification Search
USPC .................................................... 128/203.15
See application file for complete search history.

(56) References Cited

U.S. PATENT DOCUMENTS 6,089,228 A    7/2000  Smith
7,810,494 B2   10/2010 Harmer
(Continued)

FOREIGN PATENT DOCUMENTS

WO      9609085 A1    3/1996
WO      2008051621 A2 5/2008
WO      2009092434 A2 7/2009

*Primary Examiner* — Bradley Philips
*Assistant Examiner* — Victoria Leszczak
(74) *Attorney, Agent, or Firm* — Michael Mazza

(57) ABSTRACT

A powder aerosolization apparatus comprises a housing comprising an outlet adapted to be inserted into a user's mouth and one or more bypass air openings. A receptacle support within the housing supports a receptacle containing a powder pharmaceutical formulation. A puncturing mechanism within the housing creates in the receptacle one or more inlet openings and one or more powder outflow openings, wherein the powder outflow openings have a total area of from 0.2 $mm^2$ to 4.0 $mm^2$. Upon a user's inhalation through the outlet, air flows through the one or more bypass air openings and through the receptacle to aerosolize the powder pharmaceutical formulation in the receptacle. In one version, the relative flow parameters between the flow through the one or more bypass openings and the one or more powder outflow openings are selected so that flow of aerosolized pharmaceutical formulation does not occur until a predetermined inhalation flow rate is achieved.

17 Claims, 18 Drawing Sheets

(52) U.S. Cl.
CPC .... *A61M 15/0021* (2014.02); *A61M 15/0028* (2013.01); *A61M 15/0041* (2014.02); *A61M 15/0045* (2013.01); *A61M 15/0093* (2014.02); *A61M 2202/064* (2013.01)

(56) References Cited

U.S. PATENT DOCUMENTS

| | | | |
|---|---|---|---|
| 2004/0168687 A1* | 9/2004 | Asking | A61M 15/0045 128/203.15 |
| 2007/0181123 A1* | 8/2007 | Houzego | A61M 15/0045 128/203.15 |
| 2009/0308390 A1* | 12/2009 | Smutney | A61M 15/0028 128/203.15 |
| 2010/0108058 A1 | 5/2010 | Glusker | |

* cited by examiner

AEROSOLIZATION APPARATUS FOR INHALATION PROFILE-INDEPENDENT DRUG DELIVERY

BACKGROUND

Inhalable drug delivery, where an aerosolized pharmaceutical formulation is orally or nasally inhaled by a patient to deliver the formulation to the patient's respiratory tract, has proven to be a particularly effective and/or desirable alternative to other forms of drug delivery. Many types of inhalation devices exist including devices that aerosolize a dry powder pharmaceutical formulation.

One type of dry powder inhalation device aerosolizes a pharmaceutical formulation that is stored in a unit dose receptacle, such as a capsule or a blister package. A dose or a portion of a dose of a dry powder pharmaceutical formulation may be stored in the receptacle, and the receptacle may be inserted into an aerosolization device which is capable of removing the dry powder from the receptacle and aerosolizing the pharmaceutical formulation. In capsule-based dry powder inhalers, the capsule itself is often used to help effectively aerosolize the powder.

In another type of dry powder inhaler, the dry powder may be contained within a receptacle that is integrated within the device or that is insertable into the device. In this type of device, the receptacle is stationary within the device. One particular type of insertable receptacle is a blister pack. In one form, a blister pack is insertable into a passive dry powder inhaler where a user's inhalation is used to aerosolize the powder, an example of which is described in US Patent Application Publication 2010/0108058 (Glusker et al.), which is incorporated herein by reference in its entirety for all purposed. In another form, a blister pack is insertable into an active dry powder inhaler where additional energy is used for aerosolization, such as the one described in U.S. Pat. No. 5,740,794, where compressed air is released to provide the powder aerosolization energy. U.S. Pat. No. 5,740,794 is also incorporated herein by reference in its entireties for all purposes.

In all types of dry powder inhalers, the size and quality of the dose delivered to the user is dependent on the amount and condition of aerosolizable pharmaceutical formulation that exits the device. In conventional dry powder inhalers, the amount and condition of the aerosolizable pharmaceutical formulation may vary from use to use and/or from user to user. For example, often powder may exit a receptacle in agglomerated form creating particles that are too large to be effectively and consistently administered to the respiratory tract.

The effectiveness and consistency of the aerosolization and deagglomeration of the powder depends in large part on the inhalation energy provided, which is often provided by the user's inhalation. If there is not a sufficiently high flow rate through the receptacle, there is a risk that the powder will not be effectively and consistently deagglomerated into desirably sized particles. The required inhalation energy for powder fluidization and dispersion is dependent on the nature of the formulation, and in particular the adhesive forces of the drug particles to carrier particles, walls of the inhaler, or other drug particles.

There has been considerable focus recently on the adverse impact that incorrect inhaler use has on disease management in patients with asthma, chronic obstructive pulmonary disease (COPD), and other respiratory diseases. Improved training is viewed as important. Written instruction alone, as provided in the instructions for use, is viewed as inadequate. Verbal instruction is better, but this necessitates dedicated resources, which are becoming increasingly difficult to realize in a cost-constrained market. Thus, there is a need for an engineered device which requires minimal training, and minimizes the impact of poor inhaler technique on aerosol performance.

Some inhaler errors are defined as critical if they can substantially impact dose delivery to the lungs. In a large study involving 3811 patients, it was found that about half of the subjects had at least one such critical error. Critical errors may be classified into three categories: (a) failure-to-use errors; (b) dose preparation errors, and; (c) dose inhalation errors.

Failure-to-use errors are related to a number of diverse factors. Poor regimen compliance, also known as adherence, is common to all therapeutic areas. Poor compliance does not correlate with age, socioeconomic status, sex, disease severity, risk of death or knowledge of disease. Failure-to-use errors include simply forgetting, a desire to not be on a regular medication, a failure to understand the importance of regular therapy, or a feeling of well being (no longer need the drug). There are also failure-to-use errors related to the costs of treatment, and the complexity of the treatment regimen, which may require the patient to inhale multiple medications from multiple devices, multiple times daily. Fixed dose combinations comprising bronchodilators and inhaled corticosteroids in a single inhaler (e.g., Advair®, GSK), simplify the treatment regimen, thereby improving patient compliance. Fixed dose combinations comprising once daily medicines may further help in this regard.

Dose preparation errors are related to the number and complexity of steps required to prepare the dose to be inhaled. These errors are highly device dependent. Poor device compliance may be due to a lack of competence (i.e., the inability to use the device correctly) or contrivance (i.e., having the competence to use the device correctly, but contriving to use it in a manner that fails to effectively deliver drug to the lungs). In their simplest form, device use instructions may be "open-inhale-close", where the inhalation maneuver triggers dose preparation (i.e., breath actuation). In currently marketed multi-dose dry powder inhalers (MD-DPI), an additional step to prepare the dose is required. In Diskus® (Glaxo Smith Kline), this involves moving a lever, while in Turbuhaler® (Astra-Zeneca), it requires a twist of the device. Optimally, devices must be developed with the intended patient population, dose and regimen in mind. For example, a three step "open-inhale-close" device is impractical for the delivery of tobramycin to cystic fibrosis patients, owing to the large nominal dose.

Dose inhalation errors include device-independent and device-dependent errors. Device-independent errors include errors related to the instructions for use (e.g., failure to exhale before inhalation, and failure to breath-hold). These are in fact, the two most common critical errors observed. Device-dependent errors include errors related to variations in the inhalation profile (e.g., peak inspiratory flow rates too low to achieve effective powder deagglomeration), inhaled volumes too small to empty the powder contents from a receptacle, or poor coupling of the inhalation profile to the powder emptying event from a receptacle.

Poor adherence is common to all therapeutic areas. Poor adherence may result from simply forgetting to take a dose, or psychological/cognitive factors such as: a desire to not be on a regular medication, a failure to understand the importance of regular therapy, or a feeling of well-being (no longer needing the drug). Confidence that the dose has been delivered as intended via visual, auditory, or other sensory feedback has been the subject of various schemes. In some cases, the rapid onset of a pharmacologic effect provides direct confirmation of drug delivery. The situation is far more complex for the delivery of an inhaled corticosteroid from a multi-dose dry powder inhaler. In this case, there is no immediate pharmacologic effect, and sensory feedback is also limited. Dose confirmation must rely on indirect measures of pressure, or airflow through the device. Such measurements carry the risk of false positives. The more reliable an inhaler and drug combination, especially one wherein particle delivery is largely independent of flow rate, ramp time, inhaled volume and peak inspiratory flow, can substantially mitigate the types of patient errors that lead to a requirement for adherence or compliance monitoring.

Parameters which define the inhalation profile are shown in FIG. 1. Subjects use muscles in their diaphragm to create a negative pressure in the inhaler. The maximum inspiratory pressure (MIP) is not strongly correlated with the severity of lung disease. A better correlation is observed with a subject's age, with the youngest and oldest of subjects unable to generate as high a MIP. While patients may be able to generate high MIP values when asked to inhale forcefully through a device, they will often later revert to breathing comfortably through a device in practice.

The peak inspiratory flow rate (PIF) depends on the subject's inspiratory effort (e.g., forceful or comfortable as described above) and the resistance of the device. The relationship between device resistance (R), pressure drop across the inhaler ($\Delta P$), and flow rate (Q) is given by equation 1:

$$Q = \frac{\sqrt{\Delta P}}{R} \quad (1)$$

Other parameters in the inhalation profile include the inhaled volume (Vi), the ramp time to 60% of peak flow ($t_{60}$), and the total inhalation time ($t_t$). The inhaled volume varies with a subject's age and the severity of their disease. One consideration for a device is that there is sufficient inhaled volume to deliver the dispersed powder to the bronchial airways. This includes airflow to empty the powder from the powder receptacle, and sufficient chase air to deposit the drug past the subject's oropharynx (mouth and throat). The ramp time is another consideration for devices, such as blister-based devices, in which powder emptying from the receptacle occurs very early in the inhalation profile, before peak flow rates have been established. Often powder emptying is complete before peak flows and optimal dispersing energy is attained within the device.

Therefore, it is desirable to provide a device or a particulate powder formulation/inhaler device combination which reduces dose inhalation errors. In this regard, it is still further desirable to provide aerosol delivery to a patient's lungs which is largely independent of the subject's inhalation profile in terms of ramp rate to peak flow, flow rate, and inhaled volume.

It is also desirable to be able to aerosolize a powder pharmaceutical formulation in a consistent manner. It is also desirable to be able to aerosolize a pharmaceutical formulation in a highly deagglomerated form and/or with improved aerosol characteristics. It is further desirable to assure deagglomeration and improved aerosol characteristics in an easily manufacturable and usable aerosolization device. It is still further desirable to provide an aerosolization device that affords improved matching of peak inhalation flow to powder aerosolization and receptacle emptying resulting in a greater amount of powder being emptied during the highest inhalation flow rates, thus providing greater dispersion energy and concomitant better lung delivery. It is still further desirable to be able to accomplish the above in a blister-based, passive dry powder inhaler.

SUMMARY

The present invention satisfies one or more of these needs.

In one aspect of the invention, a powder aerosolization apparatus comprises a housing comprising an outlet adapted to be inserted into a user's mouth and one or more bypass air openings. A receptacle support within the housing is capable of supporting a receptacle containing a powder pharmaceutical formulation, and a feedtube is in communication with the outlet and adapted to transport aerosolized powder from the receptacle to the outlet. A puncturing mechanism within the housing creates in the receptacle one or more inlet openings and one or more powder outflow openings, wherein the powder outflow openings have a total area of from 0.2 $mm^2$ to 4.0 $mm^2$. The outlet is in fluid communication with the one or more powder outflow openings and with the one or more bypass air openings so that upon a user's inhalation through the outlet, air flows through the one or more bypass air openings and through the receptacle to aerosolize the powder pharmaceutical formulation in the receptacle, wherein a ratio of airflow through the one or more powder outflow openings to the airflow through the one or more bypass openings at peak inhalation is from 1:10 to 1:40. In one version of the invention, the relative flow resistance between the flow through the one or more bypass openings and the one or more powder outflow openings is selected so that flow of aerosolized pharmaceutical formulation through the one or more powder outflow openings does not occur until a predetermined inhalation flow rate is achieved.

In another aspect of the invention, a method of aerosolizing a dry powder pharmaceutical formulation comprises providing a housing comprising an outlet in flow communication with one or more bypass openings, the outlet also being in flow communication with a receptacle, the receptacle containing an aerosolizable powder pharmaceutical formulation. The method further comprises drawing air through the outlet to cause air to flow through the one or more bypass openings and through the one or more inlets in the receptacle and out the one or more powder outflow openings in the receptacle thereby aerosolizing the pharmaceutical formulation within the receptacle, wherein the one or more powder outflow openings have a total area of from 0.2 $mm^2$ to 4.0 $mm^2$. A ratio of airflow through the one or more powder outflow openings to the airflow through the one or more bypass openings is from 1:10 to 1:40. In one version of the invention, the flow of aerosolized pharmaceutical formulation through the one or more powder outflow openings does not occur until a predetermined inhalation flow rate is achieved.

In another aspect of the invention, a powder aerosolization system comprises an aerosolization device and an aerosolizable powder pharmaceutical formulation for pulmonary delivery. The powder is characterized by an inertial parameter of less than about 20,000 g $\mu m^2$ $s^{-1}$. A delivery of the powder formulation is independent of the user's inhalation profile across a pressure drop of from 1 kPa to 6 kPa, at an inhaled volume of at least 500 mL and with ramp times to 50% of peak inspiratory flow of less than about 190 milliseconds.

In another aspect of the invention, a multilayered blister package contains a powder pharmaceutical formulation and is adapted to be inserted into an aerosolization apparatus. The blister package comprises a cavity covered by a top section, the cavity containing the powder pharmaceutical formulation. The top section includes one or more inlet openings and one or more powder outflow openings, wherein the powder outflow openings have a total area of from 0.2 mm² to 4.0 mm².

TERMS

Unless otherwise noted, the following is a general definition of some of the terms used herein.

"Active ingredient", "therapeutically active ingredient", "active agent", "drug" or "drug substance" as used herein means the active ingredient of a pharmaceutical, also known as an active pharmaceutical ingredient (API).

"Fixed dose combination" as used herein refers to a pharmaceutical product that contains two or more active ingredients that are formulated together in a single dosage form available in certain fixed doses.

"Solids Concentration" refers to the concentration of active ingredient(s) and excipients dissolved or dispersed in the liquid solution or dispersion to be spray-dried.

"Drug Loading" refers to the percentage of active ingredient(s) on a mass basis in the total mass of the formulation.

"Mass median diameter" or "MMD" as used herein means the median diameter of a plurality of particles, typically in a polydisperse particle population, i.e., consisting of a range of particle sizes. MMD values as reported herein are determined by laser diffraction (Sympatec Helos, Clausthal-Zellerfeld, Germany), unless the context indicates otherwise.

"Mass median aerodynamic diameter" or "MMAD" as used herein refer to the median aerodynamic size of a plurality of particles, typically in a polydisperse population. The "aerodynamic diameter" is the diameter of a unit density sphere having the same settling velocity, generally in air, as a powder and is therefore a useful way to characterize an aerosolized powder or other dispersed particle or particle formulation in terms of its settling behaviour. The aerodynamic particle size distributions (APSD) and MMAD are determined herein by cascade impaction, using a NEXT GENERATION IMPACTOR™.

"Emitted Dose" or "ED" as used herein refers to an indication of the delivery of dry powder from an inhaler device after an actuation or dispersion event from a powder unit. ED is defined as the ratio of the dose delivered by an inhaler device to the nominal or metered dose. The ED is an experimentally determined parameter, and may be determined using an in vitro device set up which mimics patient dosing. It is sometimes also referred to as the Delivered Dose (DD). The ED is determined using a drug specific method such as high pressure liquid chromatography.

"Emitted Powder Mass" or "EPM" as used herein refers to the mass of a powder that is delivered from an inhaler device after an actuation or dispersion event from a powder unit. The EPM is measured gravimetrically.

"Inertial parameter" refers to the parameter which characterizes inertial impaction in the upper respiratory tract. The parameter was derived from Stoke's Law and is equal to $\rho d_{ae}^2 Q$, where $\rho$ is the particle density (also referred to as the envelope mass density), $d_{ae}$ is the aerodynamic diameter, and Q is the volumetric flow rate.

"Fine particle mass" or "FPM" as used herein means the mass of powder below a specified minimum aerodynamic size relative to the nominal dose. For example, $FPM_{<3.3\ \mu m}$ refers to the percentage of the nominal dose which has an aerodynamic particle size less than 3.3 μm, while $FPM_{S4-F}$ refers to total mass deposition on stages 4, 5, 6, 7 and the filter. FPM values are determined gravimetrically using cascade impaction, either on an ANDERSEN™ cascade impactor, or a NEXT GENERATION IMPACTOR™ cascade impactor.

"Fine particle dose" or "FPD" as used herein means the mass of an active ingredient below a specified minimum aerodynamic size relative to the nominal dose, or may simply be expressed as the mass of active agent on specific stage groupings. For example, $FPD_{<3.3\ \mu m}$ refers to the percentage of the nominal dose which has an aerodynamic particle size less than 3.3 μm, while $FPD_{S4-F}$ refers to total mass deposition on stages 4, 5, 6, 7 and the filter. FPD values are determined with a drug specific method using cascade impaction, either on an ANDERSEN™ cascade impactor, or a NEXT GENERATION IMPACTOR™.

"Upper Respiratory Tract" refers to the human anatomy comprising the nose, sinuses, pharynx, and larynx. For oral inhalation it is also referred to as the oropharynx, or the mouth-throat region.

"Lower Respiratory Tract" refers to the human anatomy comprising the trachea, upper bronchi, and lungs. The lungs are often subdivided into bronchial airways and alveoli.

"Lung Dose" refers to the percentage of active ingredient(s) which make it past the idealized Alberta mouth-throat. Data can be expressed as a percentage of the nominal dose or the emitted dose.

"Passive dry powder inhaler" refers to a powder inhaler that uses a patient's inspiratory effort to fluidize and disperse bulk powder into an aerosol. In contrast, an active dry powder inhaler uses a mechanism in the apparatus as at least a portion of generator of the aerosol.

"Rugosity" as used herein is a measure of the surface roughness of an engineered particle. For the purposes of this invention, rugosity is calculated from the specific surface area obtained from BET measurements, true density obtained from helium pycnometry, and the surface to volume ratio obtained by laser diffraction (Sympatec), viz:

$$\text{Rugosity} = (SSA \cdot \rho_{true})/S_v$$

where Sv=6/D32, where D32 is the average diameter based on unit surface area. Increases in surface roughness are expected to reduce interparticle cohesive forces, and improve targeting of aerosol to the lungs. Improved lung targeting is expected to reduce interpatient variability, and levels of drug in the oropharynx and systemic circulation. In one or more embodiments, the rugosity (Sv) may be any value within the range of 3 to 20, such as from 4 to 18, or 5 to 10, or 6 to 8.

DRAWINGS

These features, aspects, and advantages of the present invention will become better understood with regard to the following description, appended claims, and accompanying drawings which illustrate exemplary features of the invention. However, it is to be understood that each of the features can be used in the invention in general, not merely in the context of the particular drawings, and the invention includes any combination of these features, where:

DESCRIPTION

The present invention relates to an aerosolization apparatus and powder formulation for inhalation. In particular, the invention relates to a dry powder aerosolization apparatus capable of aerosolizing a pharmaceutical formulation contained in a receptacle, such as a multi-layered blister package. Although the apparatus and process is illustrated in the context of aerosolizing a dry powder pharmaceutical formulation for inhalation, the apparatus of the present invention can be used in other processes and should not be limited to the examples provided herein.

Figure 1:
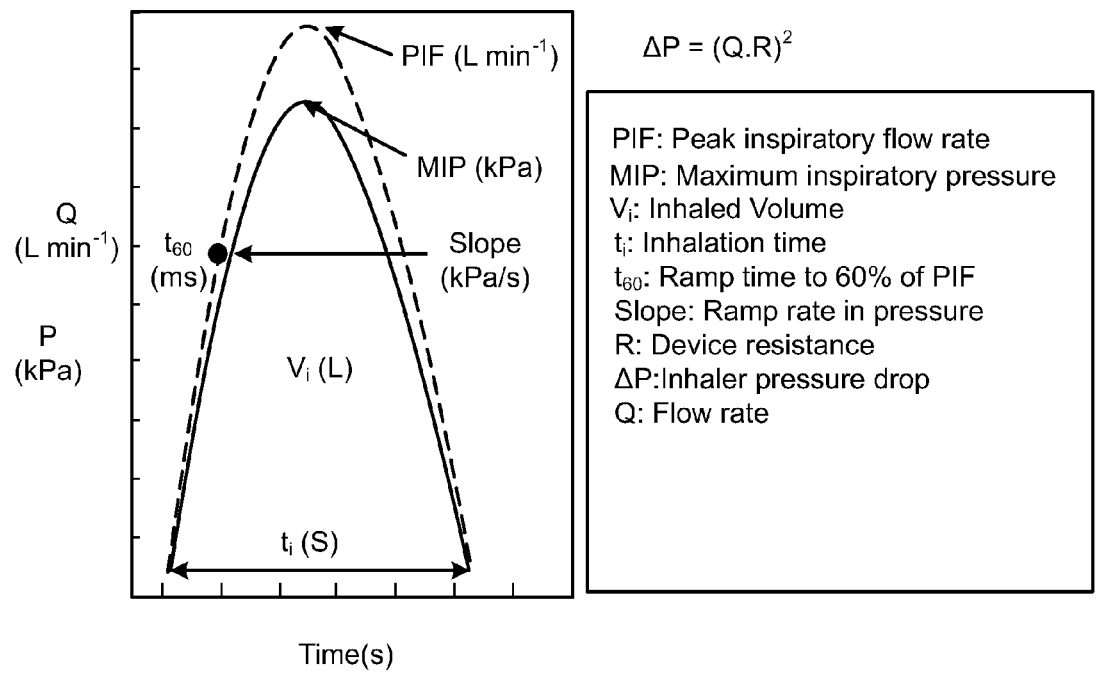
FIG. 1 is a schematic drawing showing relationships of variables in a hypothetical subject's inhalation profile.
Figure 2A:
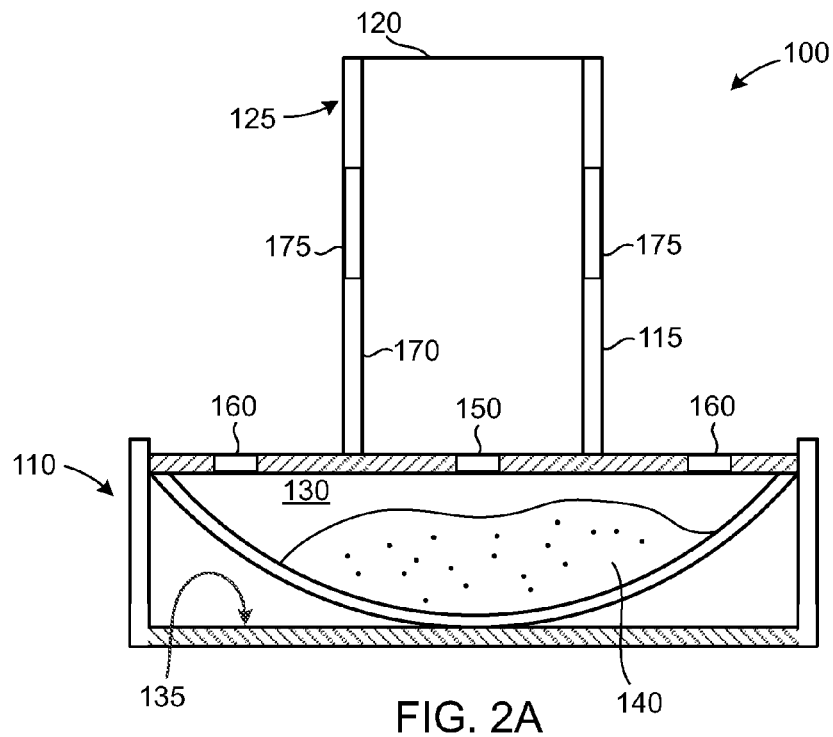
FIG. 2A is a schematic sectional side view of a version of an aerosolization apparatus according to embodiments of the invention.

An aerosolization apparatus 100 according to the present invention is shown schematically in FIG. 2A. The aerosolization apparatus 100 comprises a housing 110 which includes a conduit portion 115 including an outlet 120 that forms a mouthpiece 125. The conduit portion 115 may constitute a feedtube that is in flow communication with the outlet 120. Also within the housing 110 is a receptacle support 135 that supports a receptacle 130 containing a powder pharmaceutical formulation 140. The powder pharmaceutical formulation is made up of discrete powder particles which consist of or comprise one or more active agents and that are sized to be aerosolizable and deliverable to a user's respiratory tract.

In the version shown, the outlet 120 is sized and shaped to form a mouthpiece 125 that may be insertable into a user's mouth so that the user can inhale through the mouthpiece to cause air to flow through the aerosolization apparatus 100. Alternatively, the outlet 120 may be designed to be received in a user's nose or may be connectable to an adapter. Alternatively, the outlet 120 may be attachable to any other conduit or to a source of vacuum so that airflow is generated by something other than the user's inhalation.

The receptacle 130 that contains the powder pharmaceutical formulation 140 is provided with one or more powder outflow openings 150 and one or more receptacle inlets 160. The one or more powder outflow openings 150 in the receptacle 130 are in communication with a feedtube 170 within the conduit 115 that leads to the outlet 120. Also in communication with the conduit 115 and the outlet 120 are one or more bypass inlets 175 through which bypass air may flow. Bypass air is inhalation flow through the apparatus that bypasses the receptacle 130.

Figure 2B:
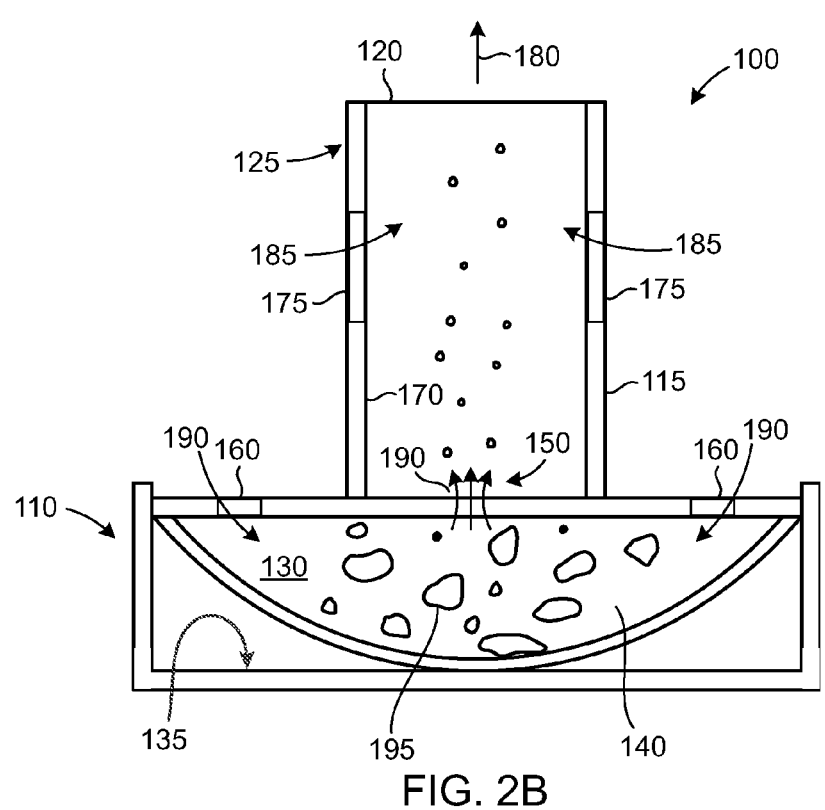
FIG. 2B is a schematic sectional side view of the apparatus of FIG. 2A in use.

As shown in FIG. 2B, when a user inhales 180 through the mouthpiece 125, a vacuum is generated that causes air to be drawn through the one or more receptacle inlets 160 and through the one or more bypass inlets 175. This generates a bypass flow of air 185 and a receptacle flow of air 190. As the receptacle flow of air 190 flows into the receptacle 130 it flows through the inlets 160 and out through the one or more outflow openings 150. This receptacle flow entrains powder 140 in the receptacle 130 and the powder becomes an aerosolized pharmaceutical formation that is dispersed in the receptacle flow 190. The aerosolized powder that is entrained in the airflow is delivered through the one or more outflow openings 150 and then through the feedtube 170 and conduit 115 to the outlet 120 where it is administered to the user during the user's inhalation.

Outside air is allowed to flow through the apparatus through two primary paths. The first path is the receptacle flow 190 and is made up of air flow that flows through the receptacle 130 itself, with air coming into the one or more inlets 160 and out through the one or more outflow openings 150, such as a center hole formed in the top of the receptacle, and into the feed tube 170. This receptacle flow 190 of air draws in the fluidized powder from the receptacle 130. The receptacle flow 190 then goes up through the feed tube 170, through an optional orifice in the feed tube 170 and into the user's respiratory tract for delivery to the deep lungs. As the powder-laden air exits through the one or more openings 150, the larger particles are fluidized and deagglomerated to create a fine aerosol suitable for deposition in the deep lung.

The second path is made up of the bypass flow 185 of air which is designed to reduce the overall resistance of the apparatus and to improve user comfort. The bypass flow 185 also serves as a way to modulate powder dispersion and airflow through the receptacle. In this regard, the overall resistance of the apparatus is usually less than 0.22 (cm $H2O)^{1/2}$/liter/minute (LPM), such as less than 0.15 (cm $H2O)^{1/2}$/LPM, or less than 0.10 (cm $H2O)^{1/2}$/LPM, and in one version can range from 0.15 to 0.21 (cm $H2O)^{1/2}$/LPM, or from 0.16 to 0.20 (cm $H2O)^{1/2}$/LPM, or from 0.17 to 0.19 (cm $H2O)^{1/2}$/LPM. In another embodiment, the overall resistance of the apparatus is lower, such as from 0.03 to 0.10 (cm $H2O)^{1/2}$/LPM. The bypass flow resistance can be adjusted to alter the flow characteristics in the device and to change the ratio of bypass flow to blister flow.

The bypass air enters the apparatus and passes through a plurality of holes, shown schematically as openings 175 in FIGS. 2A and 2B. The actual openings may be placed in other regions of the apparatus. For example, the bypass flow 185 may be made up of one or more different flow paths through the device that each bypass the receptacle 130. In one version, bypass flow 185 includes a flow in a receptacle puncturing mechanism that also serves to focus the central flow of aerosol, as described in US Patent Application Publication 2010/0108058. The number of holes may be any integer from 1 to 10, such as 1 or 2 or 3 or 4. The hole diameter is sufficient to admit the required volume of air, and typically ranges from 0.9 mm to 2.0 mm, such as from 0.9 mm to 1.4 mm, or 1.0 mm to 1.3 mm. The holes, however, need not be round, although round holes are relatively easy to manufacture and configure.

In one version, the apparatus 100 may be configured so that leak paths are minimized and/or optimized to provide acceptable or optimal performance of the apparatus 100. Contributors to aerosol performance are the ratio of receptacle flow 190 to total flow (e.g., controlled by the size of the bypass holes in the receptacle puncturing mechanism as discussed above), the size and shape of the one or more openings 150, the size and shape of the feedtube 170, and the size and shape of any other openings for bypass flow 185 and/or receptacle flow 190. By way of non-limiting example, the flow ratio between receptacle flow and bypass flow can be from 1:10 to 1:60. In another embodiment the flow ratio is from 1:10 to 1:50. In another embodiment the flow ratio is from 1:10 to 1:40.

It has been discovered that by proper selection of the size and shape of the one or more outflow openings 150 in the receptacle 130, the agglomerates 195 can be deagglomerated into sufficiently sized particles 200 that can then be effectively administered to the user's lungs during the user's inhalation, as shown in FIG. 2B. In one aspect of the invention, opening size need not serve as a physical barrier to large agglomerates. Instead, by tailoring or configuring the size and shape of the one or more outflow openings 150, the receptacle flow 190 can be controlled during the user's inhalation so that it occurs or mostly occurs when a desirably high flow rate has been achieved by the user. Thus, at the beginning of inhalation, when the flow rate is low and is ramping up, substantially only bypass flow 185 is occurring due to the high flow resistance of the flow path for the receptacle flow 190. As a result, there is little or no aerosolization that occurs early in the inhalation. Only at a point of desirably high flow rate and thus desirably high aerosolization energy does receptacle flow 190 occur. By aerosolizing the powder mostly at flows above 50% of the maximum flow rate and/or the peak inhalation flow, a greater amount of powder 140 is aerosolized from the receptacle 130 and the greater dispersion energy more effectively and consistently deagglomerates the powder into proper sized particles thereby improving lung delivery. Control of the powder emptying event enables improved coupling of device mechanics to the inspiratory flow profile, improving powder dispersion and reducing the potential for differences in lung deposition with differences in ramp rates to peak flow. Control of receptacle and bypass flows along with powder properties (e.g. primary particle size, density, rugosity) enable tuning of variations of powder dispersion with flow rate, ultimately enabling aerosol lung delivery which is independent of flow rate in-vivo.

Figure 3A:
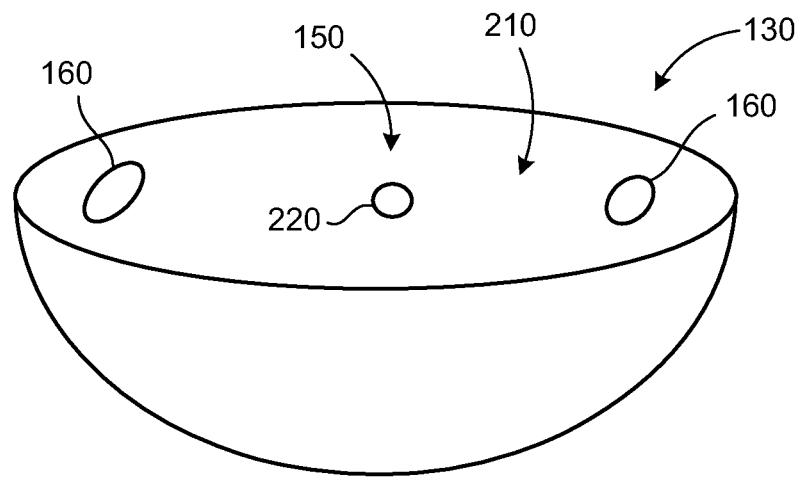
FIG. 3A is a schematic perspective view of a version of a receptacle according to embodiments of the present invention.
Figure 3B:
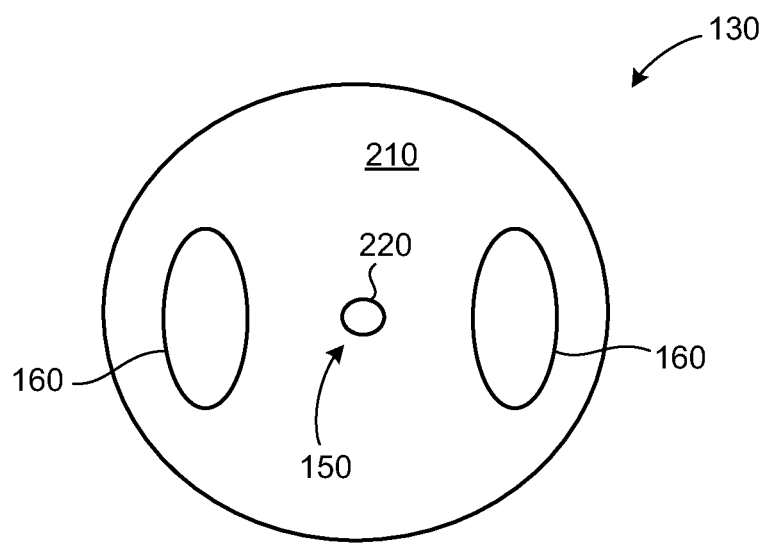
FIG. 3B is a top view of the receptacle of FIG. 3A.

An example of a receptacle 130 in accordance with one version of the present invention is shown in schematic form in FIG. 3A, and a top view is shown in FIG. 3B. In the version shown, the receptacle 130 has a bowl shape. Alternatively, the receptacle could have any other shape, such as a block, cube, cylinder, inverted pyramid, or elongated trough or valley. The receptacle also has a top section 210 that may be flat or otherwise shaped. In the version shown, the one or more receptacle inlets 160 and the one or more outflow openings 150 are formed in the top section 210.

The size and shape of the one or more outflow openings 150 is designed to allow the opening to serve as an aerosolized powder deagglomerator. In the version shown in FIGS. 3A and 3B, the one or more outflow openings 150 comprise a single, generally round opening 220 having a diameter of from about 0.8 mm to about 1.2 mm. As discussed above, it has been unexpectedly discovered that by properly selecting the size and shape of the one or more outflow openings 150, the onset of receptacle flow can occur during a portion of the inhalation so that improved deagglomerated aerosolization can be achieved.

Figure 4A:
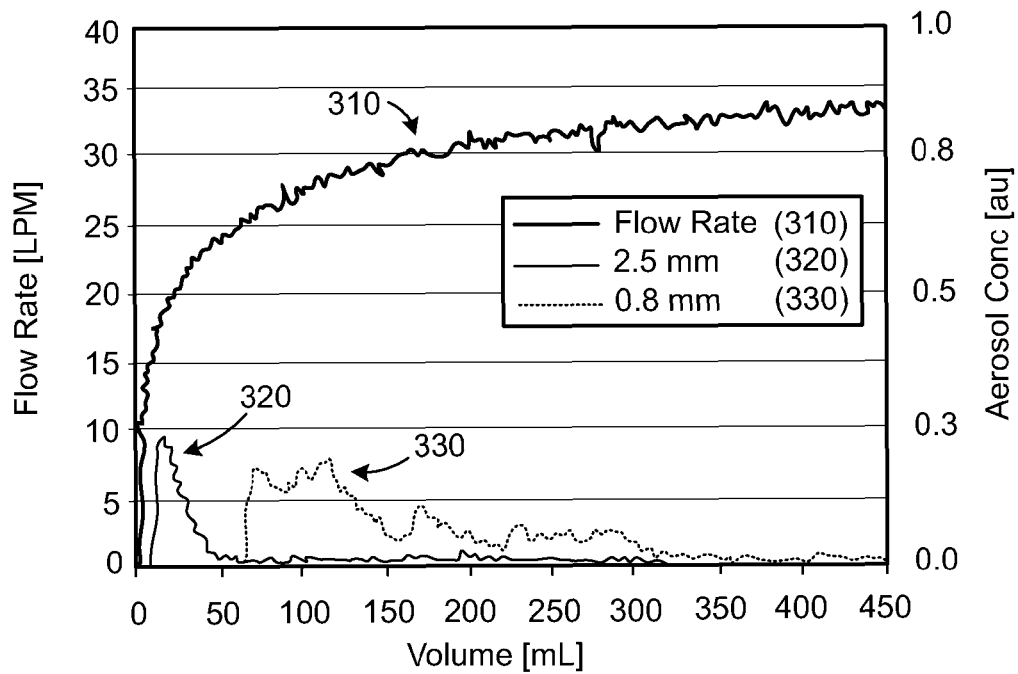
FIG. 4A is a graph showing aerosol concentration of two apparatus designs in relation to inhalation flow rate with inhalation flow rate expressed in terms of liters per minute.

The graph of FIG. 4A illustrates the desirable affects achieved by the present invention. FIG. 4A show three curves. The first curve 310 shows a representative in vitro flow rate. Curve 320 shows the aerosol concentration associated with the flow rate 310 when using a device with an outflow opening diameter of 2.5 mm (i.e. an area of 4.9 $mm^2$), such as the one in US 2010/0108058. Curve 330 shows the corresponding aerosol concentration when using a device according to the present invention, such as the one shown in FIGS. 3A and 3B with a round 0.8 mm diameter (i.e. 0.5 $mm^2$ area) outflow opening 150.

As can be seen from the graph of FIG. 4A, with the outflow opening of 2.5 mm diameter or with an area of 4.9 $mm^2$, aerosolization begins nearly at the onset of inhalation, whereas for the same bypass flow to receptacle flow arrangement but the smaller outflow opening of 0.8 mm diameter (0.5 $mm^2$), the onset of aerosolization occurs when the inhalation flow rate reaches a desired level. In this manner, the aerosolization occurs when the inhalation flow is sufficiently high to provide sufficiently high dispersion energy to more effectively and consistently deagglomerate and/or fluidize the powder pharmaceutical formulation 140. Thus, by utilizing an aerosolization apparatus 100 according to an embodiment of the present invention, the need for a trigger valve, threshold valve, or other mechanism for delaying aerosolization can be reduced or eliminated.

Figure 4B:
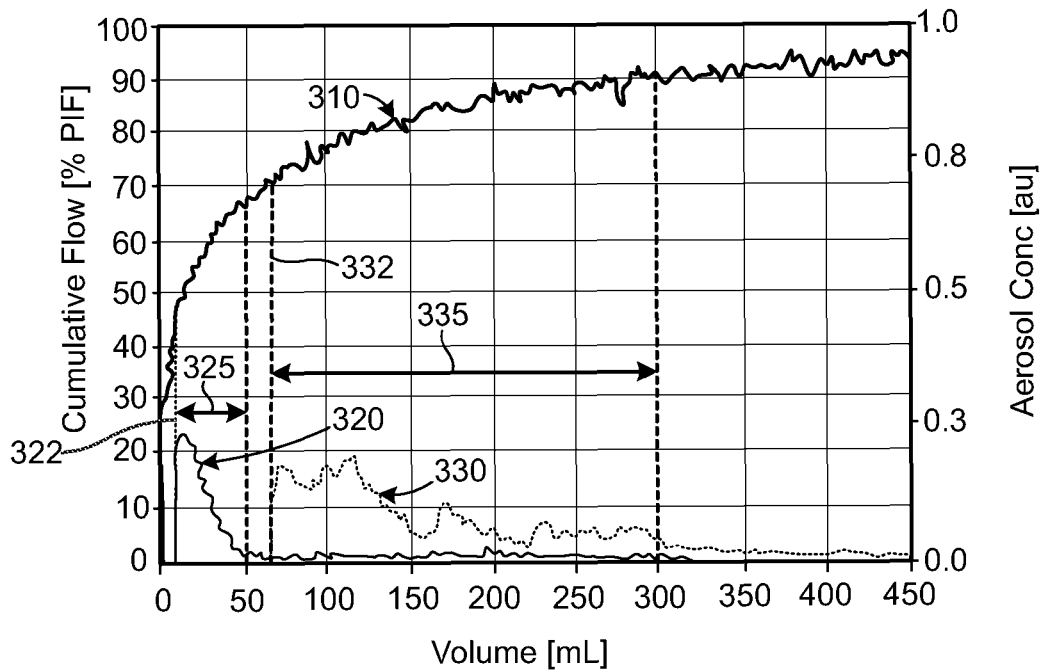
FIG. 4B is a graph showing aerosol concentration of two apparatus designs in relation to inhalation flow rate with inhalation flow rate expressed in terms of percentage of peak inhalation flow.

FIG. 4B shows a similar graph as in FIG. 4A, but expresses the flow rate in terms of percentage of peak inspiratory flow (PIF). As can be seen in FIG. 4B, the onset 322 of aerosolization in the 4.9 mm$^2$ opening begins at a flow of less than 50% of PIF (about 40% to 49% as shown in FIG. 4B). The onset of aerosolization 332 is shown for an inhaler device in accordance with embodiments of the present invention and comprising a 0.5 mm$^2$ opening. Thus aerosolization 332 occurs when the flow is greater than 50% of PIF, such as about 65% to 68% of the PIF as shown by FIG. 4B.

Accordingly, in one aspect of the invention, the one or more outflow openings 150 are sized and shaped so that the onset of aerosolization and/or fluidization of the pharmaceutical formulation begins at a desired inhalation flow rate that is at least 50% of the PIF for the user's inhalation. In one or more embodiments the one or more outflow openings 150 are sized and shaped so that aerosolization and/or fluidization of the pharmaceutical formulation begins at an inhalation flow rate of at least 55% or 60% or 65% or 70% or 75% or 80% or 85% of the maximum inhalation flow rate. In one version, the size and shape of the one or more outflow openings 150 is selected so that aerosolization and/or fluidization begins after an inhalation flow rate of at least 50% of PIF or 55% or 60% or 65% or 70% or 75% of PIF.

As can also be seen in FIGS. 4A and 4B, not only does the onset of aerosolization begin at a desirable flow rate, the powder emptying process is also lengthened and occurs over a greater portion of the inhalation maneuver. More specifically, the aerosolization period 325 for the 2.5 mm opening occurs during the first 50 ml of inhalation. In contrast, the aerosolization period 335 for the 0.8 mm opening occurs across more than 200 ml of inhalation, all of which is at a higher flow rate than any of the aerosolization for the 2.5 mm opening device. Accordingly, an increased portion of the aerosolization process occurs during the flatter portion of the inhalation flow rate. The resulting powder emptying is thus less dependent on the user's ability to ramp quickly (i.e. to have a sufficiently steep inhalation flow rate curve) to peak flow. This is particularly important for users suffering from lung diseases, such as asthma and/or COPD, where their ramp rate may be compromised. With the present invention, consistent aerosolization and delivery occurs over inhalation volumes and rates that can be achieved by these patients. The present invention provides effective aerosolized drug delivery that is powered by a user's inhalation but that is largely independent of the user's breathing profile.

Though the area of the opening may vary slightly depending on the shape of the one or more outflow openings 150, in one or more embodiments of the present invention, effective delay of aerosolization and/or effective deagglomeration can be achieved when the one or more outflow openings 150 have an opening with an area of 4.5 mm$^2$ or less or with an area of 4 mm$^2$ or less. In one or more embodiments, the area of the opening in an outlet will be 3.2 mm$^2$ or less, 1.8 mm$^2$ or less, from 0.2 mm$^2$ to 1.8 mm$^2$, or from 0.4 mm$^2$ to 1.2 mm$^2$. As one of ordinary skill in the art would recognize, the sizes and shapes of the one or more outflow openings 150 in accordance with the present invention may need to be altered depending on the overall dimensions and geometry of the aerosolization device and depending on the relative proportions of bypass air flow 185 to receptacle air flow 190. The above sizes have been determined to be advantageous for bypass air flow to receptacle air flow ratios of from about 50:1 to 10:1. In some embodiments a ratio of bypass air flow to receptacle air flow is 40:1 or 35:1 or 30:1 or 25:1 or 20:1 or 15:1 or 10:1.

Figure 5A:
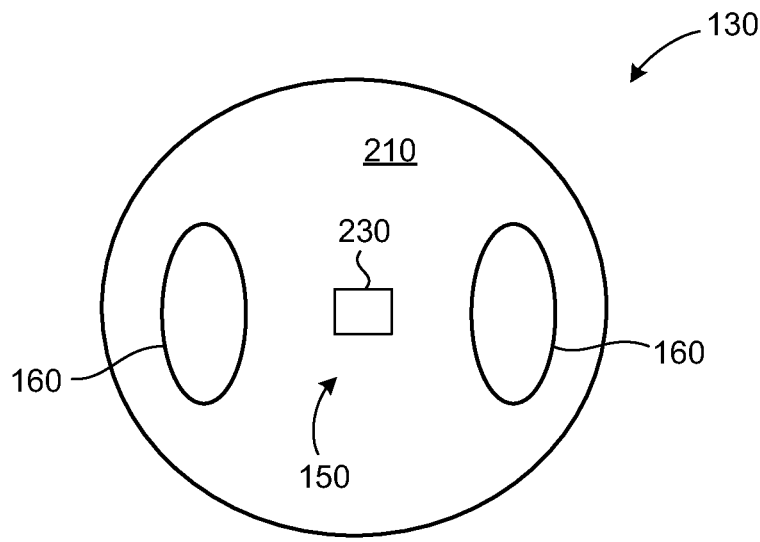
FIGS. 5A through 5G are schematic top views of alternative versions of receptacles according to embodiments of the present invention.
Figure 5B:
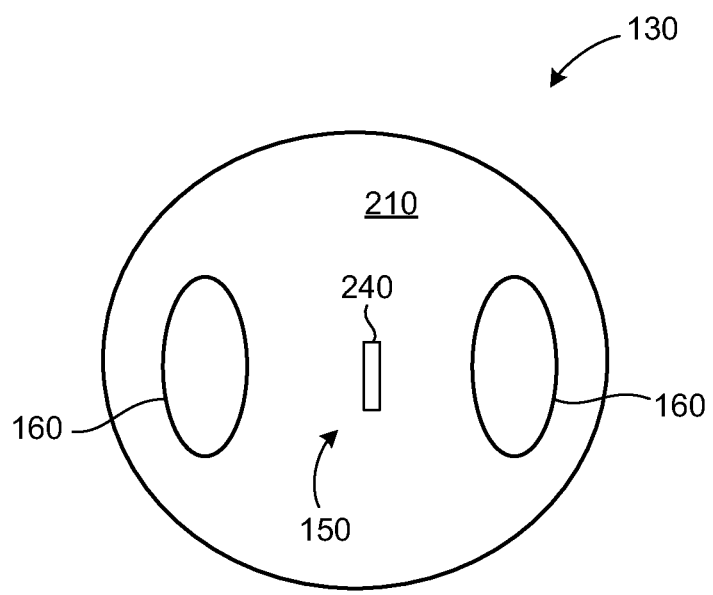

In the version of FIGS. 3A and 3B, the one or more outflow openings 150 is shown as a single rounded opening 220. A rounded outlet 220 in accordance with the present invention has a diameter of about 2 mm or less when approximately circular or a major diameter of 2.5 mm or less when oval. FIGS. 5A and 5B show top views of an alternative receptacle where the one or more outflow openings 150 is shown as a square 230 or rectangle 240. In the square version of FIG. 5A, the length of the sides should be 2 mm or less. In the rectangular version, the length of the longest side should be 5 mm or less. Other shapes, such as triangular, oval, elliptical, star-shaped, or any other shape opening may additionally and/or alternatively be used. Whatever shape is used, the area of the opening of each outlet will preferably fall within the area ranges described above.

Figure 5C:
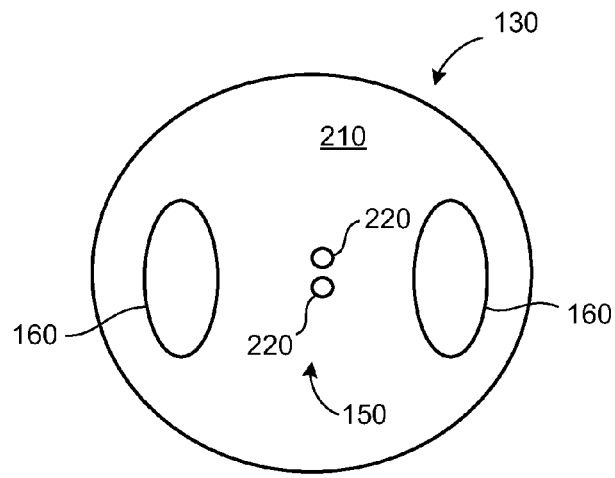
Figure 5D:
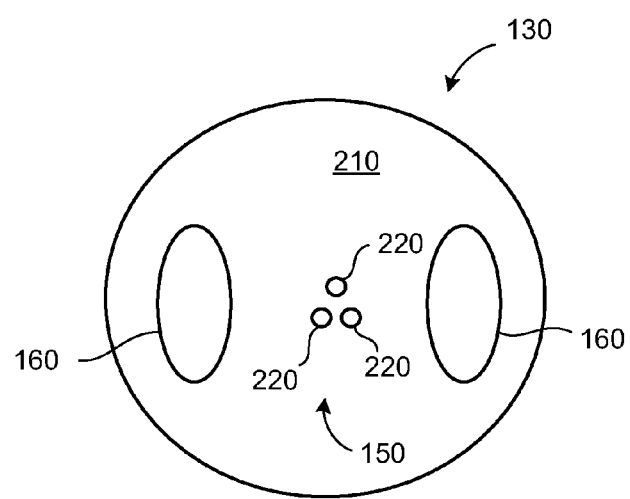
Figure 5E:
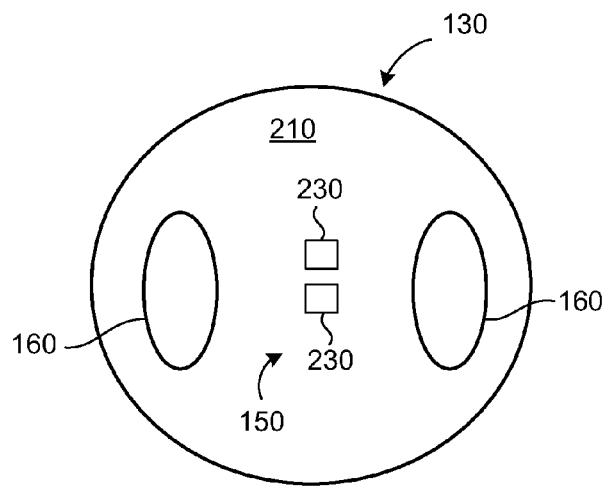
Figure 5F:
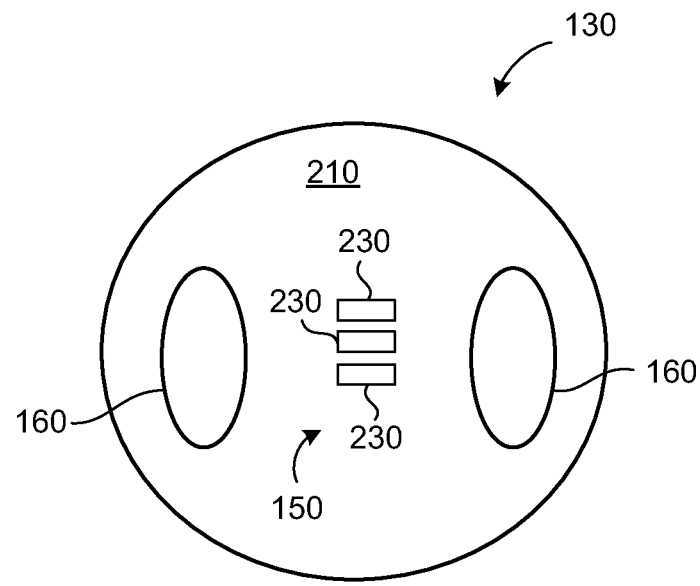
Figure 5G:
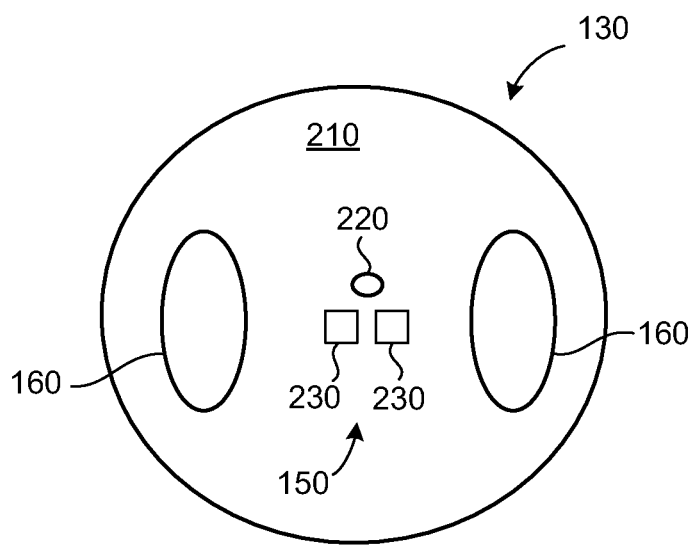

Alternative and/or additional receptacle opening shapes or configurations are shown in FIGS. 5C through 5G. In each of these versions, the one or more outflow openings 150 comprise a plurality of openings. In the version of FIG. 5C, the one or more outflow openings 150 comprises two rounded openings 220. In the version of FIG. 5D, the one or more outflow openings comprises three rounded outlets 220. FIGS. 5E and 5F show square or rectangular outflow openings 230. FIG. 5G shows a combination of outflow opening shapes.

It has been further discovered that overall aerosol delivery performance can be improved by properly selecting the total area of the one or more outflow openings 150 in relation to the bypass flow and receptacle flow arrangement. By selecting an appropriate value for the total area, the flow resistance of the receptacle flow portion of the flow through the device can be tailored so as to improve aerosolization performance. As a result aerosolization of the powder may be delayed or otherwise made to occur when a desirable airflow has been achieved. Thus, a user will be required to generate a sufficiently high vacuum that will provide sufficient energy to properly aerosolize the powder pharmaceutical formulation in the receptacle 130. By making the one or more outflow openings 150 sufficiently small, consistent aerosolization can be maintained with no need for flow controlling devices such as trigger valves and flow regulators. Thus, in accordance with one version of the invention, the one or more outflow openings 150 in the receptacle 130 is sized so that the total area of all of the openings in the one or more outflow openings 150 will have an area of 4 mm$^2$ or less. In one or more embodiments, the total area of all of the outflow openings 150 is 3.2 mm$^2$ or less, 1.8 mm$^2$ or less, from 0.2 mm$^2$ to 1.8 mm$^2$, or from 0.4 mm$^2$ to 1.2 mm$^2$.

In some versions, the receptacle 130 is a chamber integrated into the aerosolization apparatus 100. In this version, the apparatus may be a single use device with the aerosolizable pharmaceutical formulation 140 pre-contained within the receptacle 130. The openings can be created prior to use by puncturing the top section 210 to create the one or more receptacle inlets 160 and the one or more outflow openings 150. Alternatively, the one or more receptacle inlets 160 and/or the one or more outflow openings 150 can be preformed and sealed, with the seal being removable just prior to use.

Figure 6A:
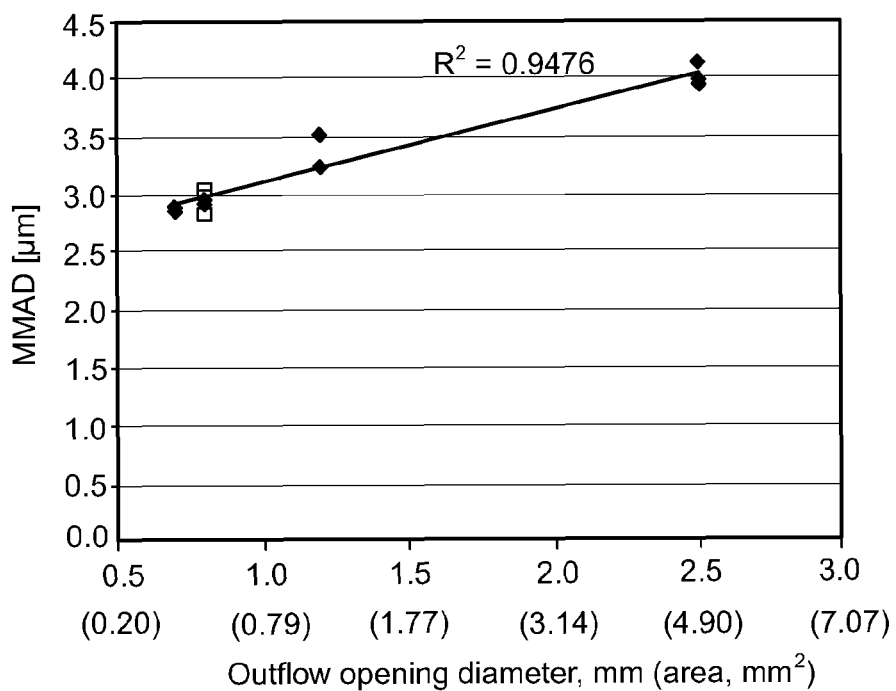
FIG. 6A is a graphical representation of the MMAD resulting from different outflow opening sizes.
Figure 6B:
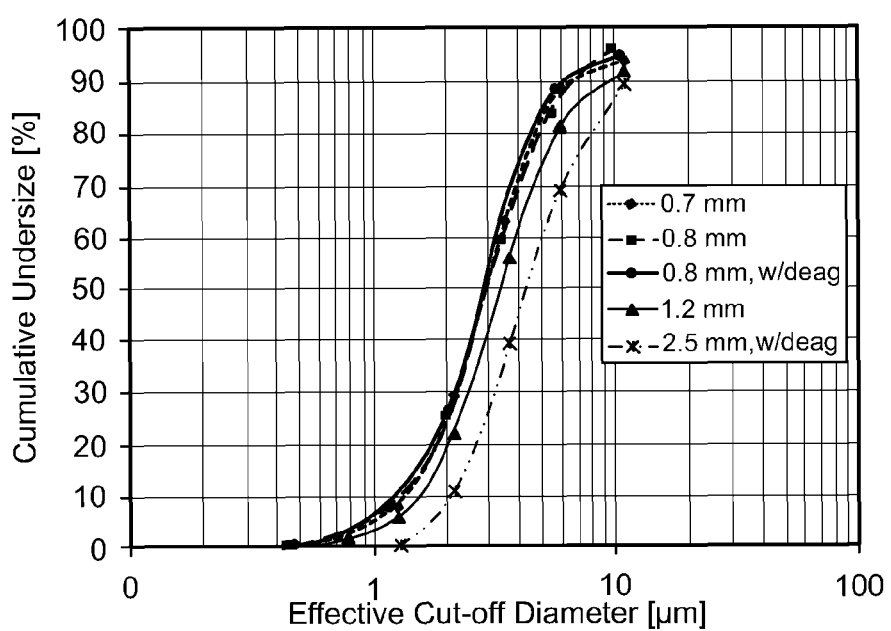
FIG. 6B is a graphical representation of aerodynamic particle size distributions for particles generated using various versions of the present invention.

The effectiveness of one or more embodiments of the present invention is illustrated in FIGS. 6A and 6B. FIG. 6A shows a graph of the corresponding MMAD of the powder exiting the device for various receptacle opening 150 sizes. As can be seen, for a given ratio of flow rates between bypass flow and receptacle flow, the smaller the opening size, the lower the MMAD, indicating that the aerosolized powder using the smaller opening sizes has a higher concentration of small particles which therefore means that a greater percentage of the pharmaceutical formulation is deliverable to the deep lungs. FIG. 6B shows the aerodynamic particle size distribution for particles using a 0.7 mm diameter (0.38 mm$^2$) opening, a 0.8 mm diameter (0.5 mm$^2$) opening, a 0.8 mm diameter (0.5 mm$^2$) opening (with a downstream deagglomerator), a 1.2 mm diameter (1.13 mm$^2$) opening, and a 2.5 mm diameter (4.9 mm$^2$) opening (with a downstream deagglomerator) of the type described in US2010/0108058. As the curves shift to the left in the graph, the particles become more desirably of respirable size. Thus, it can be seen that all of the smaller openings provide significant improvement over the 2.5 mm diameter (4.9 mm$^2$) opening, even when a downstream deagglomerator is present.

The impact of variations in receptacle opening size for Apparatus 100 on powder dispersion as presented in FIG. 6A shows that the MMAD of the powder exiting the device for various receptacle opening 150 sizes decreases with decreases in receptacle opening diameter. This is the result of the relationship between the powder emptying event and the flow profile. Aerodynamic particle size distributions (APSD) were determined on a Next Generation Pharmaceutical Impactor (MSP Corp., model 170) without a preseparator. The APSD data were taken at the same device flow rate and sampling volume used to generate the corresponding EPM data. The aerosol deposited at each stage was collected on glass fiber filter substrates (Pall Life Science, P/N 60140, and 61663), which were clamped to the bottom surface of each collection cup (MSP Corp., P/N 0170-98-0210A-C). The powder mass deposited on each stage was determined by weighing the filters before and after device actuation on a microbalance. Each APSD measurement required the actuation of 6 blisters (2 mg fill mass), to provide sufficient mass on the stages for gravimetric quantitation.

Figure 7:
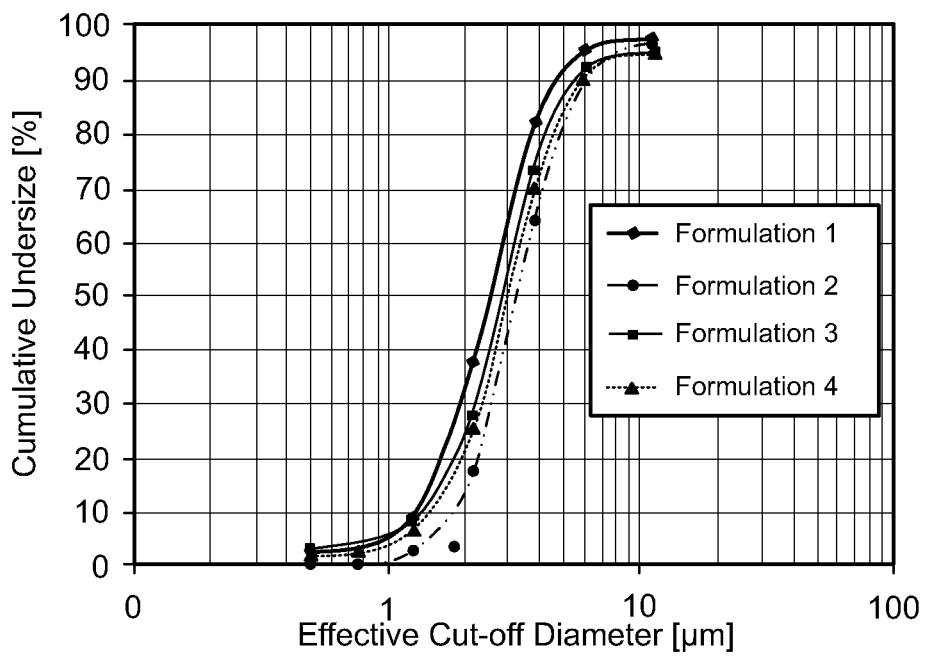
FIG. 7 is a graphical representation of aerodynamic particle size distributions for different formulations tested using the present invention.

FIG. 7 shows the aerodynamic particle size distribution when testing the device according to the present invention using four different pharmaceutical formulations. Each formulation comprised an active agent, distearoylphosphatidylcholine, and calcium chloride. As can be seen, the resulting MMADs and particle size distribution is desirably small for all four of the formulations indicating the applicability across various formulations.

The patient's inhalation maneuver applies a pressure drop across the aerosolization device 100 where a combined total airflow is drawn through two main flow channels, defined as bypass air flow 185 and receptacle flow 190 as shown in FIG. 2B. The flow resistance through the device 100 is defined by the following equation $$R = \frac{\sqrt{\Delta P}}{Q} \quad (1)$$

where
R=Resistance, cmH$_2$O$^{0.5}$ LPM$^{-1}$
ΔP=Differential pressure drop, cmH$_2$O
Q=Volumetric flow rate, LPM.
Therefore, the DPI total resistance can be derived by the following equations $$R_T = \sqrt{R_{PBL}^2 + R_I^2 + R_D^2} \quad (2)$$

and $$R_{PBL} = \frac{R_P \cdot \left(\frac{R_B \cdot R_L}{R_B + R_L}\right)}{R_P + \left(\frac{R_B \cdot R_L}{R_B + R_L}\right)} \quad (3)$$

where,
RT=Total DPI resistance
RD=Deagglomerator resistance, e.g. opening
RP=Bypass resistance
RB=Blister resistance
RL=Leak resistance
RI=Inlet resistance
If blister outlet diameter is the primary deagglomerator then the DPI resistance will be $$R_T = \sqrt{R_{PBL}^2 + R_I^2} \quad (4)$$

RP, RB and RD can be varied to achieve inhaler resistance between about 0.03 and about 0.50 cmH$_2$O$^{0.5}$ LPM$^{-1}$, more preferably between about 0.12 and about 0.30 cmH$_2$O$^{0.5}$ LPM$^{-1}$ and still maintain good aerosol performance. The relative resistances can be tailored and configured to achieve the desired aerosolization onset point as described herein.

Figure 8:
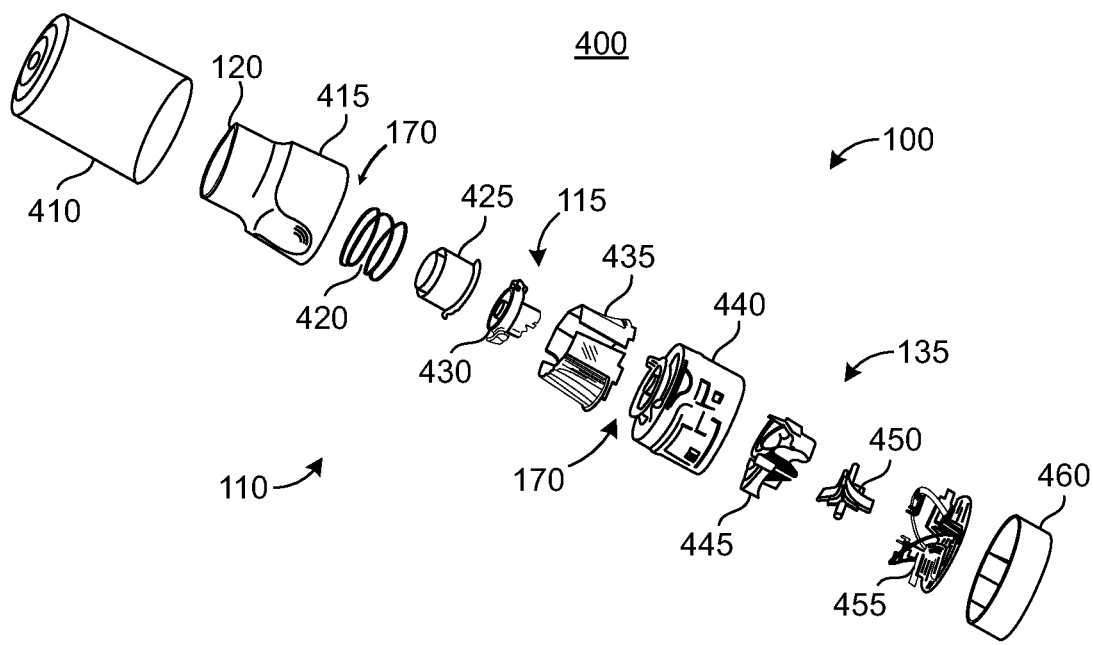
FIG. 8 is an schematic exploded view of a version of an aerosolization apparatus according to the invention.

An example of one version of a particular inhalation device 100 exemplifying the present invention will now be described. The device 100 according to this particular version 400 is shown in an exploded view in FIG. 8. The device 400 includes a cap 410, a mouthpiece 415, a compression spring 420, an optional diffuser 425, a puncture mechanism or cutter 430, a bearing 435, a body 440, a receptacle support 135 in the form of a tray 445 on which a receptacle rests, an optional flick mechanism 450 to assist in deagglomeration prior to aerosolization, a baseplate 455, and a sleeve 460. The specifics of these parts and their interactions are discussed in more detail in US patent application Publication 2010/0108058 (Glusker et al.).

Figure 9A:
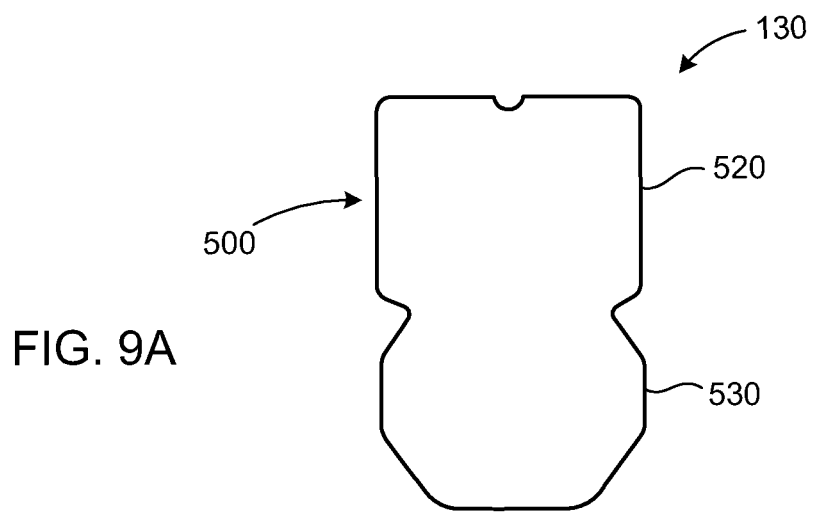
FIG. 9A is a schematic top view of a blister package receptacle according to a version of the present invention.
Figure 9B:
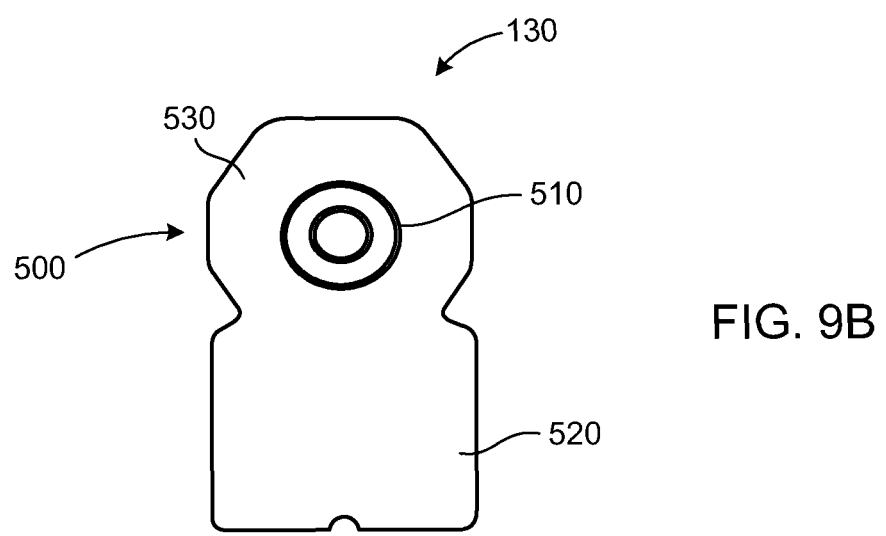
FIG. 9B is a schematic bottom view of a blister package receptacle according to a version of the present invention.
Figure 9C:
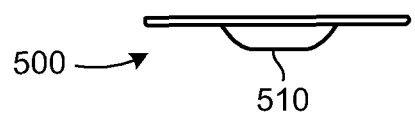
FIG. 9C is a schematic side view of a blister package receptacle according to a version of the present invention.
Figure 10A:
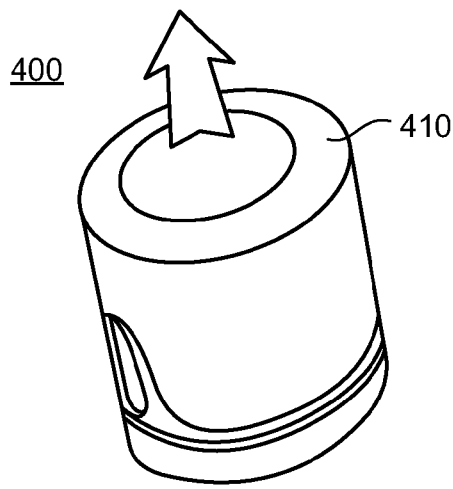
FIGS. 10A through 10F are perspective views illustrating the operation of an aerosolization apparatus according to embodiments of the present invention.
Figure 10B:
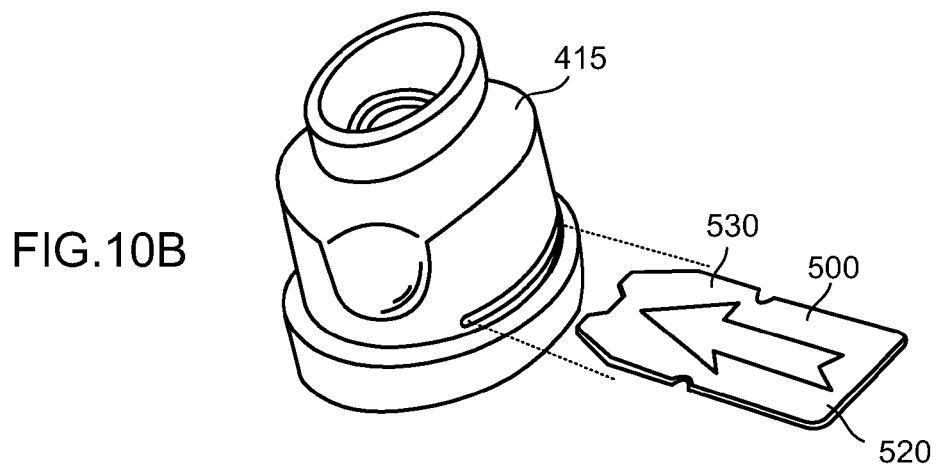
Figure 10C:
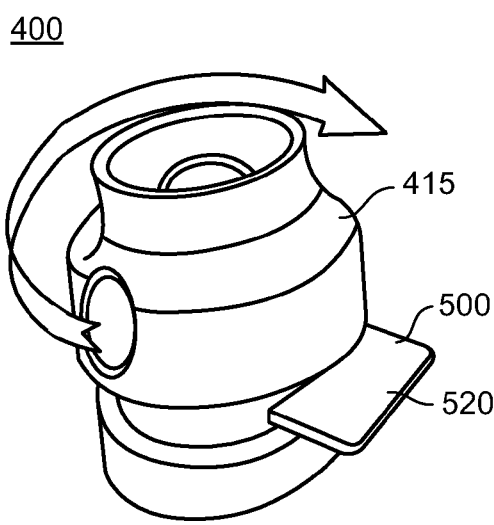
Figure 10D:
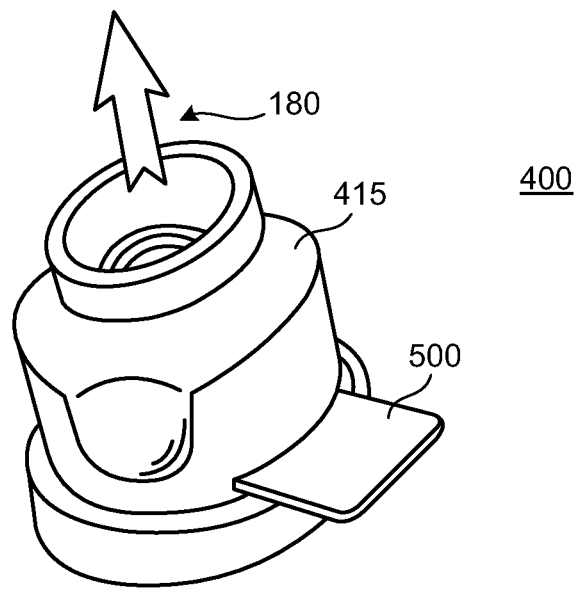
Figure 10E:
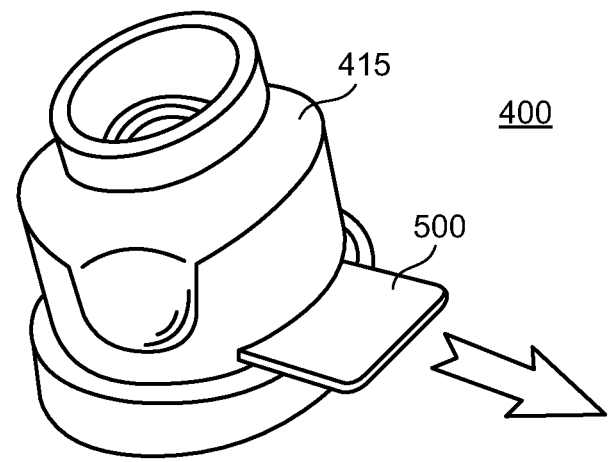
Figure 10F:
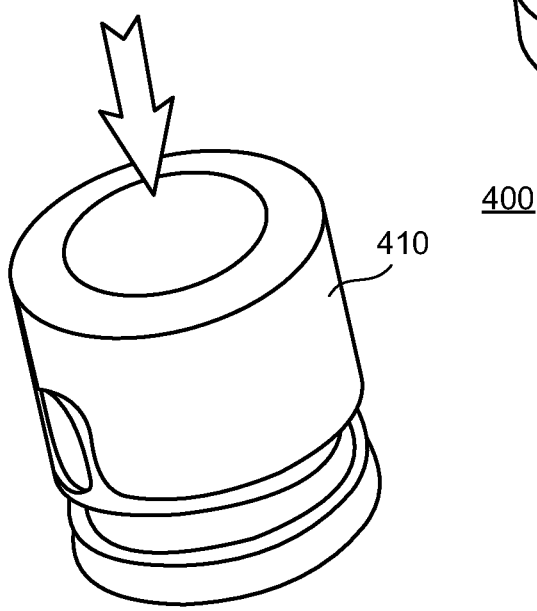

In this version of the invention, the receptacle 130 is in the form of a multi-layered blister package 500 that contains a unit dosage of powder medicament with a cavity 510, as shown in FIGS. 9A though 9C. In one version, the receptacle includes a lower foil laminate comprising a blister for holding powder and an upper foil laminate covering the lower foil laminate. Non-limiting examples of receptacle materials include those disclosed in U.S. Pat. Nos. 5,589,275 and 6,270,869, which are incorporated herein by reference. Suitable foils may be commercially available, e.g., from Alcan Inc. (Montreal, Quebec). The blister package 500 includes a graspable tab portion 520 and a front portion 530 that includes the cavity 510. Specifics on the blister package are discussed in US2010/0108058 and in U.S. Pat. No. 5,740,794, both of which are incorporated herein by reference in their entireties. The receptacle according to this version, comprises a rear portion having three perpendicular sides, a middle portion comprising notches, and a tapered front portion. The notches are capable of interacting with an interlock system, such as that described in US2010/0108058.

Figure 11:
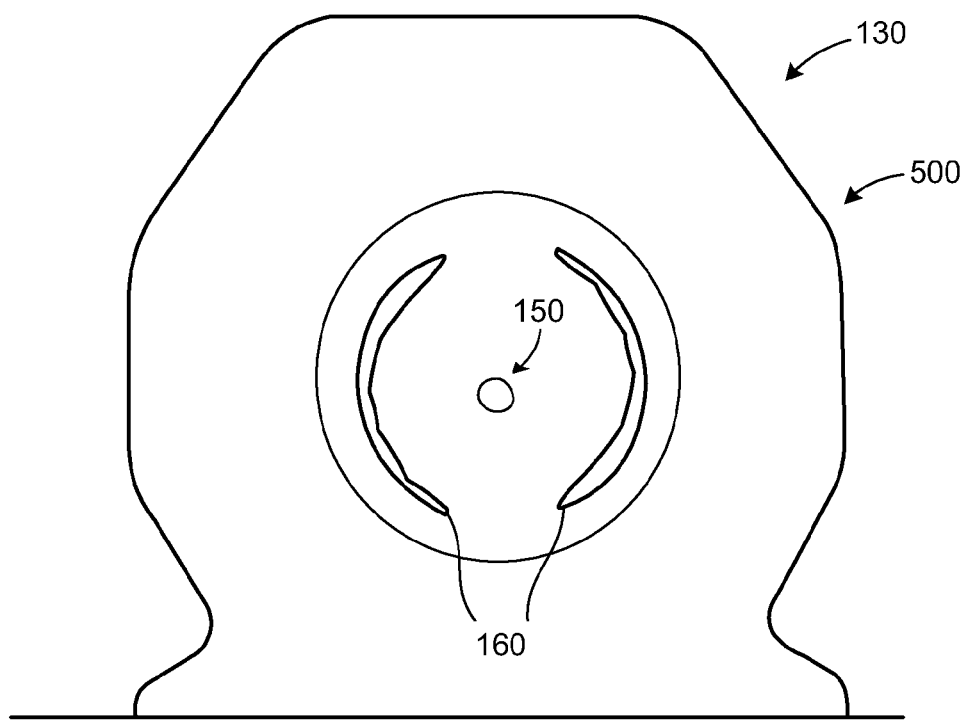
FIG. 11 is top view of inlets and an outflow opening of a punctured receptacle in accordance with one version of the present invention.
Figure 12:
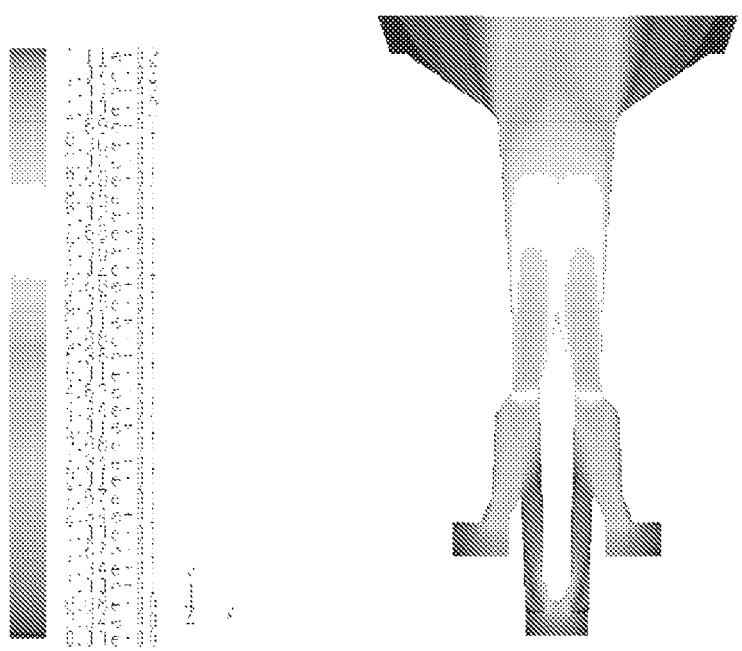
FIG. 12 is a velocity plot showing flow velocities according to a version of the present invention.

In the aerosolization device 400 according to this one aspect of the present invention, the receptable 130 in the form of a unit dose blister 500 is adapted to be nested inside the inhalation device 400, as shown in FIGS. 10A-10F. After removing the cap 410, the blister package 500 is inserted into the inhaler 400. By rotating portions of the housing 110, such as the inhaler body and base in opposite directions, this will cause a puncturing mechanism within the housing 110 to pierce open the inlet and powder outflow opening(s) in the blister 500. FIG. 11 shows a punctured blister pack 500 showing the inlets 160 and a receptacle outflow opening 150. FIG. 11 shows the side opening inlets 160 where receptacle flow 190 entrains into the blister cavity and the center opening diameter for the outflow opening 150 where drug powder is aerosolized and/or fluidized out of the blister. As patient inhales through the inhaler, the powder exiting the blister impacts the tip of the outlet hole piercer, which provides a supplemental deagglomeration via impaction. This effect is shown in FIG. 12. The blister outlet opening(s) are sized accordingly to achieve a desired air velocity, e.g. 35, 45, 55 or 65 m/s.

A blister opening means in the form of a puncturing mechanism 430 will pierce and/or tear open the inlet 160 and powder outflow opening(s) 150 of the blister 500. The blister opening means or puncturing mechanism 430 may be a wireform, or a molded member, such as molded plastic, and can even be formed as a one-piece member with one of the components of the apparatus.

In some embodiments, a puncturing mechanism comprising a tooth or teeth that is/are used to cut or tear one or more arc-shaped air inlet openings 160 in the blister 500 operates by descending, e.g., rapidly, into the drug package, then moving through an arc, and then retracting completely out of the drug package. This movement takes place in the apparatus when the user rotates one housing part of the apparatus relative to another housing part. FIG. 11 shows one non-limiting result of this action.

Another aspect of the invention comprises a feed tube 170, such as a tube member which directs air flow from the exit opening of a receptacle toward an exit or mouthpiece opening of an inhalation apparatus (shown schematically in FIGS. 2A and 2B). In some embodiment, the blister opening means or puncturing mechanism 430 may be arranged within or on the feed tube.

In use, as with the schematic version shown in FIGS. 2A and 2B, outside air is allowed to flow through the apparatus through two primary paths. The receptacle flow 190 is through the blister itself, with air coming into the air inlet openings 160 and out through the center hole 150 and into the feed tube. This air draws in the fluidized powder from the blister 500. The flow then goes up through the feed tube, through an orifice and into the user's lungs. The bypass flow 185 is for bypass air, which in one or more embodiments, may enter the apparatus and through a plurality of holes 175 that may be arranged anywhere within the housing of the device.

The invention also contemplates an arrangement wherein the receptacle is supported in a mechanism for advancing a continuous web (e.g., a strip or disk), which carries a plurality of receptacles past the fluidization location. Non-limiting examples of such devices are disclosed in U.S. Pat. No. 6,606,992, the disclosure of which is hereby expressly incorporated by reference in its entirety.

Alternatively, the one or more inlets 160 and/or the one or more outlets 150 may be pre-formed into the blister package 500 or other type of receptacle 130 prior to insertion into the aerosolization apparatus 100. In another version, the aerosolization apparatus comprises multiple doses of the pharmaceutical formulation. An example of a multi-dose inhalation apparatus is described in US Patent Application Publication 2011/0226244 (Perkins et al) which is incorporated herein by reference in its entirety.

Figure 13A:
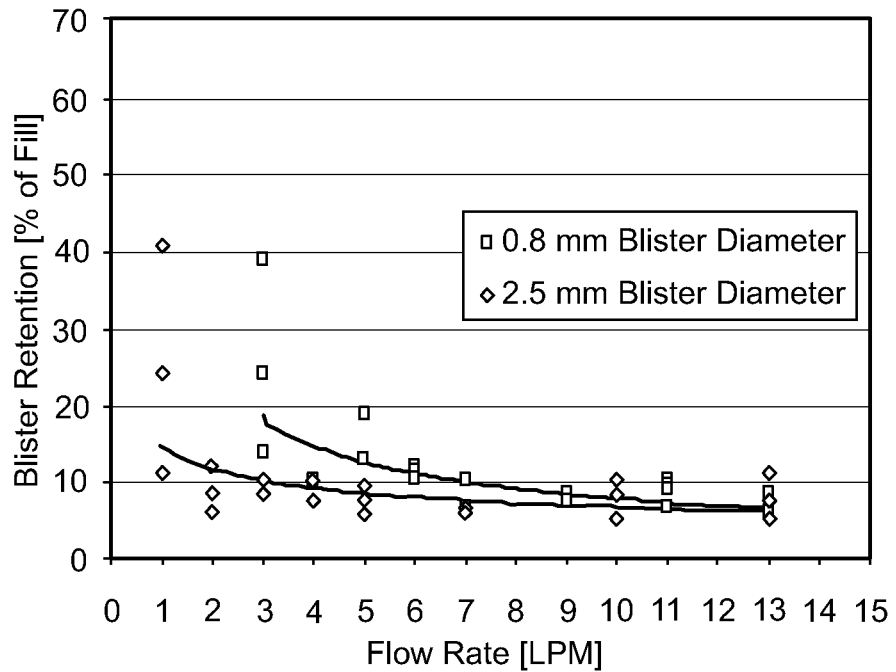
FIG. 13A is a graphical representation showing receptacle powder retention in relation to flow rate for different sized opening diameters for a 1 mg powder fill.
Figure 13B:
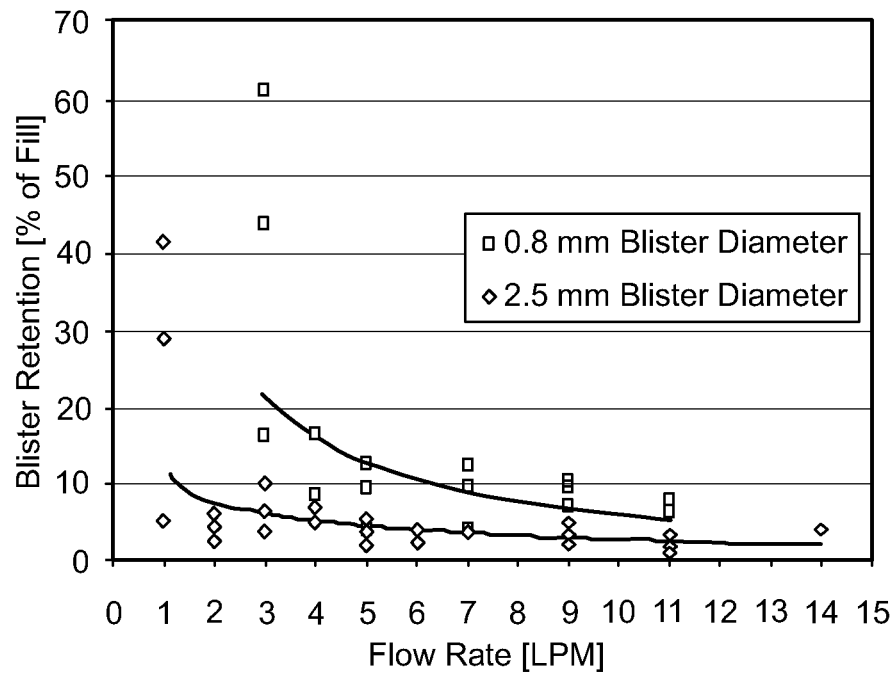
FIG. 13B is a graphical representation showing receptacle powder retention in relation to flow rate for different sized opening diameters for a 2 mg powder fill.

FIG. 13A shows the relationship between blister air flow and powder retention within the cavity 510 for a 1 mg fill mass. FIG. 13B shows the same plot for a 2 mg fill mass.

In one or more embodiments, the aerosolization apparatus 100 aerosolizes the powder medicament consistently in both size of dose delivered and aerosol quality. Powder quality may be measured as fine particle fraction, or FPF, to indicate the fraction of the aerosolized powder having particle size below a given threshold. Typically, the primary particle size is substantially smaller than the threshold used for FPF. Therefore, FPF is most often a function of fluidization or agglomeration state, or percentage distribution of particles that are single primary particles or agglomerations of multiple primary particles. Superior aerosol quality, as measured by FPF (or more precisely agglomerate state) is a function of powder fluidization and powder deagglomeration, both of which are accomplished by the devices and methods described herein.

Figure 14A:
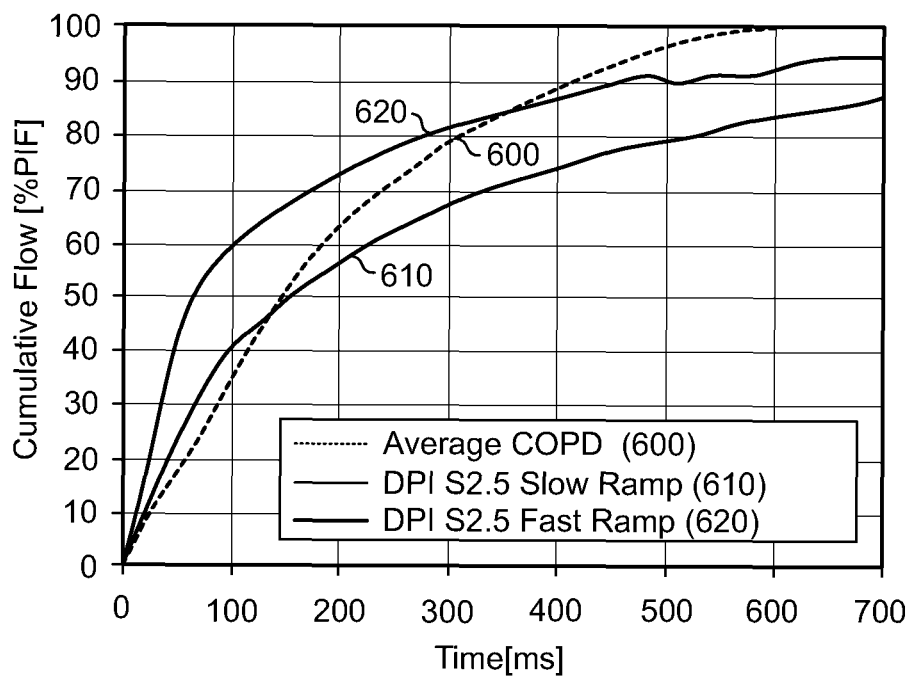
FIG. 14A is a graphical representation of representative ramp profiles for average COPD patients, slow ramp, and fast ramp profiles.
Figure 14B:
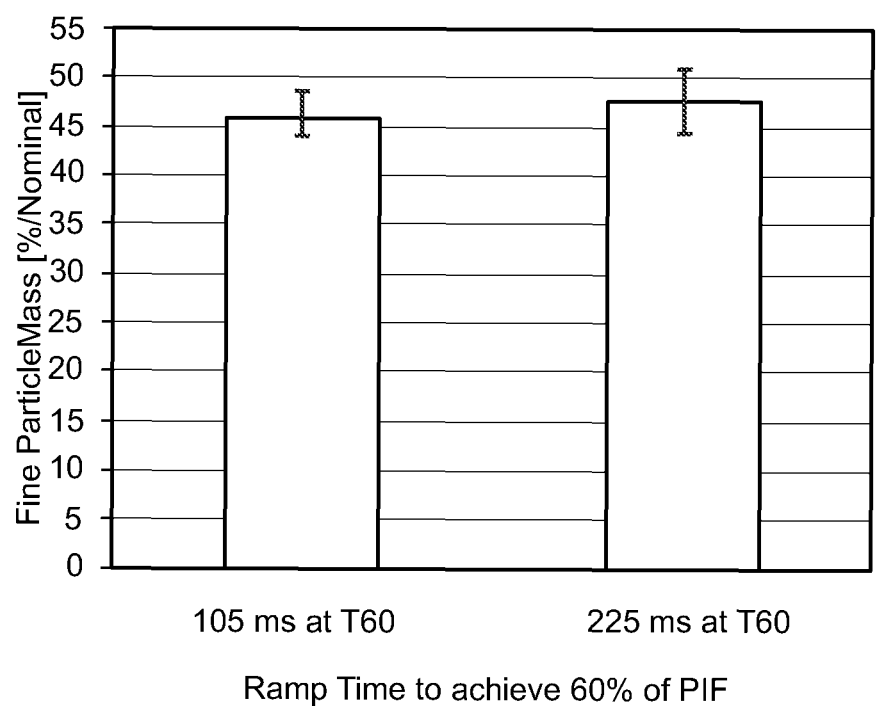
FIG. 14B is a bar chart showing the fine particle mass for two ramp times.

In one or more embodiments, efficacy of the powder aerosolization/fluidization is independent of inhalation flow and flow rate patterns. For example, FIG. 14A shows cumulative flow profiles representative of ramp profiles for average COPD ramps 600, slow ramp 610, and fast ramp 620. Ramp rate as used herein is defined as that portion of the inhalation flow rate curve with the steepest slope (highest rate of acceleration of air flow). FIG. 14B is a bar chart showing in vitro aerosol data that confirms the performance is effectively independent of ramp flow for a 1.2 mm diameter opening (1.13 mm$^2$). In FIG. 14B, fine particle mass (% nominal) is shown for two different ramp times to achieve 60% of peak inhalation flow. As can be seen, the differences in rate of flow increase (ramp rate) do not affect powder aerosolization.

Figure 15:
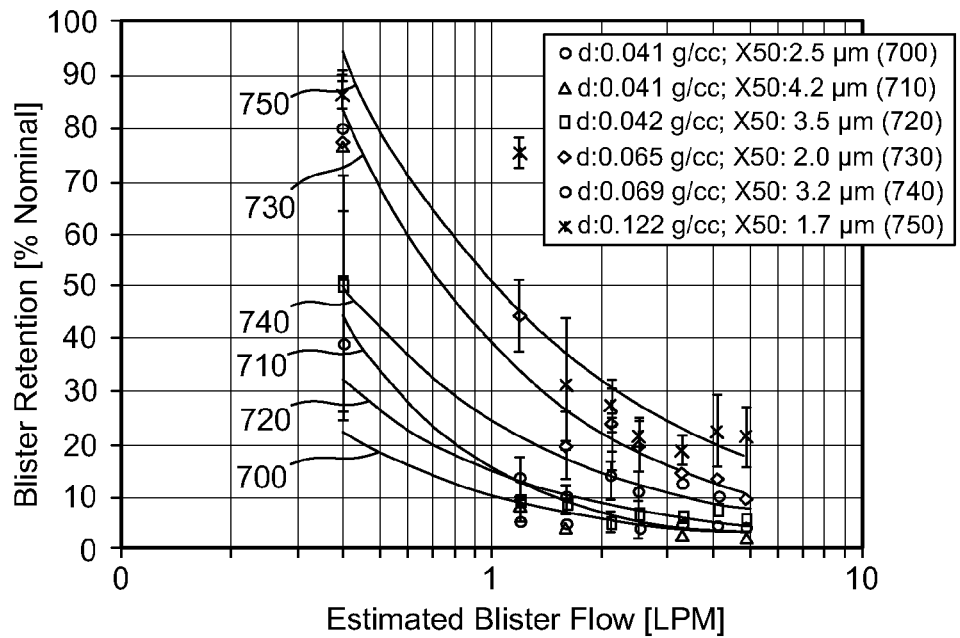
FIG. 15 is a plot showing blister retention as a function of flow rate through the blister for six different powder densities of various particle sizes.

FIG. 15 shows percent blister retention as a function of flow rate through the blister for six different porous particle powder formulations with varying powder densities and geometric particle sizes (700-750). As can be seen, blister retention is more dependent on powder density than on primary particle size. In order to achieve high blister evacuation with high density particles, higher airflow through the blister is desirable. Thus, the present invention is particularly useful with low density powders, such as those with a density less than 0.1 g/cm$^3$. FIG. 15 is discussed in more detail below in connection with the Examples.

For passive dry powder inhalers, the effectiveness and consistency of the fluidization and dispersion of the powder depends in large part on the inhalation energy provided by the user, and the physicochemical properties of the powder. If there is not a sufficiently high flow rate through the receptacle, the powder will often not be effectively and consistently fluidized and dispersed into desirably sized particles. In some embodiments, inhalation energy for powder dispersion is formulation dependent, hence, embodiments of the inhaler device combined with engineered powders of the present invention provide optimal performance, such as emitted dose performance, in the aerosolization apparatus. In particular, an emitted dose my be greater than, 40% or 45% or 50% or 55% or 60% or 65% or 70% or 75% or 80% or 85% or 90% or 95% of the nominal dose.

In one version, the powdered formulation for use in the present invention includes a dry powder formulated to have a particle size suitable for aerosolization and delivery to the respiratory tract of a user. In one version, the particles are sized and designed to permit penetration into the alveoli of the lungs. In some embodiments, the particles have a geometric size that is less than 20 μm mass median diameter (MMD). In some embodiments, the particles are less than 10 μm MMD, such as less than 9, 8, 7, 6, 5, or 4 MMD. In some embodiments, the particles are in the range of 0.1 μm to 5 μm MMD. The aerosol particle size distribution is preferably about 1.0-6.0 μm mass median aerodynamic diameter (MMAD), or about 1.5-4.5 μm MMAD or about 1.5-4.0 μm MMAD. Such powders are described U.S. Pat. Nos. 6,051,256; 6,258,341; 6,518,239; 6,582,728; 6,835,372; 7,306,787; 7,790,145; 7,628,978; 7,871,598 and in WO 95/24183, all of which are all incorporated herein by reference in their entireties. Large, light particles, particularly those with an MMD between 5 μm and 10 μm, are also suitable for use in an aerosolization apparatus according to the invention are disclosed in U.S. Pat. Nos. 5,874,064; 5,985,309; and 6,503,480, all of which are incorporated herein by reference in their entireties.

However, particle size alone does not assure effective delivery of the aerosolized pharmaceutical formulation. During the receptacle filling process and during storage, the powder pharmaceutical formulation tends to cake together, as shown in FIG. 2A. As a result of this caking and as a result of particle-to-particle interactions, during the aerosolization process particles will sometimes tend to clump together into agglomerates 195, as shown in FIG. 2B. The agglomerates are often too large to be effectively delivered to the lung and will typically remain within an aerosolization apparatus or impact a user's throat.

In some versions, the powdered formulation for use in the present invention includes a dry powder formulated to have a particle size suitable for aerosolization and delivery to the respiratory tract of a user. The upper respiratory tract (URT) includes the nose, sinuses, pharynx and larynx, while the lower respiratory tract (LRT) includes the trachea, upper bronchi, and lungs. Powder deposition in the URT following oral inhalation is governed by inertial impaction. Numerous studies have examined the relationship between deposition in the URT and the inertial parameter, $\rho d_{ae}^2 Q$ ($\rho$ is the envelope mass density, $d_{ae}$ is the aerodynamic diameter, and Q is the volumetric flow rate). Aerosol particles which do not impact within the URT are assumed to deposit within the lungs. To achieve mean URT deposition of less than about 40% of the delivered dose, the inertial parameter should be less than about 20,000 g μm$^2$ s$^{-1}$. In one version, it is desired that the inertial parameter be less than 10,000 or 8,000 g μm$^2$ s$^{-1}$, so as to maximize lung deposition. In the context of the present invention, achieving target values of the inertial parameter is achieved via control of the physicochemical characteristics of the dry powder and adjustments of powder dispersion within the aerosolization apparatus.

An in-vitro measure of total lung deposition is provided by using casts of human upper respiratory tracts obtained via imaging. The idealized Alberta cast is thought to provide a measure of the mean deposition in the URT anticipated in-vivo. Delivery post-URT is assumed to be a reasonable in-vitro measure of total lung deposition. Deposition post-URT in the idealized Alberta cast of human upper respiratory tracts should be greater than 50% of the nominal dose, preferably greater than 60% or 70% of the nominal dose. The anatomy of the URT differs significantly from subject to subject. These anatomical variations are responsible in large part for the high variability in lung delivery observed with current marketed aerosol products.

For delivery to the LRT (lungs), the particles should have a primary particle size (mass median diameter (MMD) by laser diffraction) which is less than 30 μm, preferably less than 10 μm or 5 μm, and most preferably in the range from 1 μm to 5 μm. The mass median aerodynamic diameter (MMAD) can vary with changes in device resistance and flow rate. It is generally desirable if the MMAD is in the range from about 1.0 to about 6.0 μm, as discussed above.

In a preferred version, the invention provides a system and method for aerosolizing a powder pharmaceutical formulation comprising an active agent and delivering the pharmaceutical formulation to the respiratory tract of the user, and in particular to the lungs of the user.

The active agent described herein includes an agent, drug, compound, composition of matter or mixture thereof which provides some pharmacologic, often beneficial, effect. As used herein, the terms further include any physiologically or pharmacologically active substance that produces a localized or systemic effect in a patient. An active agent for incorporation in the pharmaceutical formulation described herein may be an inorganic or an organic compound, including, without limitation, drugs which act on: the peripheral nerves, adrenergic receptors, cholinergic receptors, the skeletal muscles, the cardiovascular system, smooth muscles, the blood circulatory system, synoptic sites, neuroeffector junctional sites, endocrine and hormone systems, the immunological system, the reproductive system, the skeletal system, autacoid systems, the alimentary and excretory systems, the histamine system, and the central nervous system. Suitable active agents may be selected from, for example, hypnotics and sedatives, tranquilizers, respiratory drugs, drugs for treating asthma and COPD, anticonvulsants, muscle relaxants, antiparkinson agents (dopamine antagonists), analgesics, anti-inflammatories, antianxiety drugs (anxiolytics), appetite suppressants, antimigraine agents, muscle contractants, anti-infectives (antibiotics, antivirals, antifungals, vaccines) antiarthritics, antimalarials, antiemetics, anepileptics, bronchodilators, cytokines, growth factors, anti-cancer agents, antithrombotic agents, antihypertensives, cardiovascular drugs, antiarrhythmics, antioxicants, anti-asthma agents, hormonal agents including contraceptives, sympathomimetics, diuretics, lipid regulating agents, anti-androgenic agents, antiparasitics, anticoagulants, neoplastics, antineoplastics, hypoglycemics, nutritional agents and supplements, growth supplements, antienteritis agents, vaccines, antibodies, diagnostic agents, and contrasting agents. The active agent, when administered by inhalation, may act locally or systemically.

The active agent may fall into one of a number of structural classes, including but not limited to small molecules, peptides, polypeptides, proteins, polysaccharides, steroids, proteins capable of eliciting physiological effects, nucleotides, oligonucleotides, polynucleotides, fats, electrolytes, and the like.

In one version, the active agent may include any active pharmaceutical ingredient that is useful for treating inflammatory or obstructive airways diseases, such as asthma and/or COPD. Suitable active ingredients include long acting beta 2 agonist, such as salmeterol, formoterol, indacaterol and salts thereof, muscarinic antagonists, such as tiotropium and glycopyrronium and salts thereof, and corticosteroids including budesonide, ciclesonide, fluticasone, mometasone and salts thereof. Suitable combinations include (formoterol fumarate and budesonide), (salmeterol xinafoate and fluticasone propionate), (salmeterol xinofoate and tiotropium bromide), (indacaterol maleate and glycopyrronium bromide), and (indacaterol and mometasone).

Other examples of active agents suitable for use in this invention include but are not limited to one or more of calcitonin, amphotericin B, erythropoietin (EPO), Factor VIII, Factor IX, ceredase, cerezyme, cyclosporin, granulocyte colony stimulating factor (GCSF), thrombopoietin (TPO), alpha-1 proteinase inhibitor, calcitonin, granulocyte macrophage colony stimulating factor (GMCSF), growth hormone, human growth hormone (HGH), growth hormone releasing hormone (GHRH), heparin, low molecular weight heparin (LMWH), interferon alpha, interferon beta, interferon gamma, interleukin-1 receptor, interleukin-2, interleukin-1 receptor antagonist, interleukin-3, interleukin-4, interleukin-6, luteinizing hormone releasing hormone (LHRH), factor IX, insulin, pro-insulin, insulin analogues (e.g., monoacylated insulin as described in U.S. Pat. No. 5,922,675, which is incorporated herein by reference in its entirety), amylin, C-peptide, somatostatin, somatostatin analogs including octreotide, vasopressin, follicle stimulating hormone (FSH), insulin-like growth factor (IGF), insulintropin, macrophage colony stimulating factor (M-CSF), nerve growth factor (NGF), tissue growth factors, keratinocyte growth factor (KGF), glial growth factor (GGF), tumor necrosis factor (TNF), endothelial growth factors, parathyroid hormone (PTH), glucagon-like peptide thymosin alpha 1, IIb/IIIa inhibitor, alpha-1 antitrypsin, phosphodiesterase (PDE) compounds, VLA-4 inhibitors, bisphosphonates, respiratory syncytial virus antibody, cystic fibrosis transmembrane regulator (CFTR) gene, deoxyreibonuclease (Dnase), bactericidal/permeability increasing protein (BPI), anti-CMV antibody, 13-cis retinoic acid, macrolides such as erythromycin, oleandomycin, troleandomycin, roxithromycin, clarithromycin, davercin, azithromycin, flurithromycin, dirithromycin, josamycin, spiromycin, midecamycin, leucomycin, miocamycin, rokitamycin, andazithromycin, and swinolide A; fluoroquinolones such as ciprofloxacin, ofloxacin, levofloxacin, trovafloxacin, alatrofloxacin, moxifloxicin, norfloxacin, enoxacin, grepafloxacin, gatifloxacin, lomefloxacin, sparfloxacin, temafloxacin, pefloxacin, amifloxacin, fleroxacin, tosufloxacin, prulifloxacin, irloxacin, pazufloxacin, clinafloxacin, and sitafloxacin, aminoglycosides such as gentamicin, netilmicin, paramecin, tobramycin, amikacin, kanamycin, neomycin, and streptomycin, vancomycin, teicoplanin, rampolanin, mideplanin, colistin, daptomycin, gramicidin, colistimethate, polymixins such as polymixin B, capreomycin, bacitracin, penems; penicillins including penicllinase-sensitive agents like penicillin G, penicillin V, penicillinase-resistant agents like methicillin, oxacillin, cloxacillin, dicloxacillin, floxacillin, nafcillin; gram negative microorganism active agents like ampicillin, amoxicillin, and hetacillin, cillin, and galampicillin; antipseudomonal penicillins like carbenicillin, ticarcillin, azlocillin, mezlocillin, and piperacillin; cephalosporins like cefpodoxime, cefprozil, ceftbuten, ceftizoxime, ceftriaxone, cephalothin, cephapirin, cephalexin, cephradrine, cefoxitin, cefamandole, cefazolin, cephaloridine, cefaclor, cefadroxil, cephaloglycin, cefuroxime, ceforanide, cefotaxime, cefatrizine, cephacetrile, cefepime, cefixime, cefonicid, cefoperazone, cefotetan, cefmetazole, ceftazidime, loracarbef, and moxalactam, monobactams like aztreonam; and carbapenems such as imipenem, meropenem, pentamidine isethiouate, albuterol sulfate, lidocaine, metaproterenol sulfate, beclomethasone diprepionate, triamcinolone acetamide, budesonide acetonide, fluticasone, ipratropium bromide, flunisolide, cromolyn sodium, indacaterol, tiotropium, glyopyrrronium, ergotamine tartrate and where applicable, analogues, agonists, antagonists, inhibitors, and pharmaceutically acceptable salt forms of the above. In reference to peptides and proteins, the invention is intended to encompass synthetic, native, glycosylated, unglycosylated, pegylated forms, and biologically active fragments and analogs thereof.

Active agents for use in the invention further include nucleic acids, as bare nucleic acid molecules, vectors, associated viral particles, plasmid DNA or RNA or other nucleic acid constructions of a type suitable for transfection or transformation of cells, i.e., suitable for gene therapy including antisense. Further, an active agent may comprise live attenuated or killed viruses suitable for use as vaccines.

The amount of active agent in the pharmaceutical formulation will be that amount necessary to deliver a therapeutically effective amount of the active agent per unit dose to achieve the desired result. In practice, this will vary widely depending upon the particular agent, its activity, the severity of the condition to be treated, the patient population, dosing requirements, and the desired therapeutic effect. The composition will generally contain anywhere from about 1% by weight to about 99% by weight active agent, typically from about 2% to about 95% by weight active agent, and more typically from about 5% to 85% by weight active agent, and will also depend upon the relative amounts of additives contained in the composition. The compositions of the invention are particularly useful for active agents that are delivered in doses of from 0.001 mg/day to 100 mg/day, preferably in doses from 0.01 mg/day to 75 mg/day, and more preferably in doses from 0.10 mg/day to 50 mg/day. It is to be understood that more than one active agent may be incorporated into the formulations described herein and that the use of the term "agent" in no way excludes the use of two or more such agents.

In the context of some of the embodiments of the present invention, the volume of the receptacle, the density of the powder and the minimum fill mass that is achievable are all parameters determining the loading of active agent in the formulation. The composition will generally contain anywhere from about 0.1% by weight to about 99% by weight active agent, typically from about 0.5% to about 90% by weight active agent, and more typically from about 5% to 85% by weight active agent, and will also depend upon the relative amounts of additives contained in the composition.

These ranges capture the wide range of potencies observed for active agents. For example, asthma/COPD therapeutics are generally highly potent. Marketed active agents typically have nominal doses less than 500 mcg (micrograms), often on the order of 100 mcg, and as low as 5 mcg. For engineered powders with low densities, fill masses in blisters are typically on the order of about 0.5 mg to a maximum of about 5 mg. For a 5 mcg dose in a 0.5 mg fill mass, the drug loading is just 0.1%. This drives the lower limit. The upper limit of the range is driven by active agents which require nominal doses which are at the limit of, or greater than the limit of the fill mass (about 5 mg).

In addition to the active agent, a pharmaceutical formulation may optionally include one or more pharmaceutical excipients which are suitable for pulmonary administration. These excipients may be generally present in the composition in amounts ranging from about 5% to about 99.9% percent by weight, preferably from about 10% to about 99.5%, and more preferably from about 15% to about 99% by weight.

Such excipients may serve to further improve the features of the active agent composition, for example by providing more efficient and reproducible delivery of the active agent, or by improving the handling characteristics of the dry powders (e.g., flowability) to facilitate filling of powder into receptacles. In addition, excipient materials can often function to improve the physical and chemical stability of the active agent, to modulate interparticle cohesive forces, or to target particles to specific receptors in the lungs. One or more excipients may also be provided to serve as bulking agents when it is desired to reduce the concentration of active agent in the formulation.

The flow rate from the receptacle in aerosolization apparatus 100 is typically between 1 LPM and 10 LPM. These flow rates are fairly small in comparison with most marketed inhalers. Two-fold differences in total lung deposition have been observed for spheronized particles of budesonide in the Pulmicort® Turbuhaler® (Astra-Zeneca), when the peak inspiratory flow rate is decreased from 60 LPM to 30 LPM. Similarly, blends of asthma and COPD therapeutics with coarse lactose monohydrate generally require flow rates greater than 10 LPM to overcome adhesive forces between the drug and carrier. As a result, particles which are engineered to reduce interparticle cohesive forces are often preferred.

Pharmaceutical excipients and additives useful in the present pharmaceutical formulation include but are not limited to amino acids, peptides, proteins, non-biological polymers, biological polymers, carbohydrates, such as sugars, derivatized sugars such as alditols, aldonic acids, esterified sugars, and sugar polymers, which may be present singly or in combination. Suitable excipients are those provided in U.S. Pat. No. 6,187,344, and U.S. Pat. No. 6,582,729, which are incorporated herein by reference in their entireties. The excipient may have a glass transition temperature ($T_g$) above about 35° C., preferably above about 40° C., more preferably above 45° C., most preferably above about 55° C.

The pharmaceutical formulation may also include a buffer or a pH adjusting agent, typically a salt prepared from an organic acid or base. Representative buffers include organic acid salts of citric acid, ascorbic acid, gluconic acid, carbonic acid, tartaric acid, succinic acid, acetic acid, or phthalic acid, Tris, tromethamine hydrochloride, or phosphate buffers. Amino acid buffers (e.g., histidine, glycine) may also be suitable.

In some versions of the present invention, the formulations comprise core-shell particles, where the particle core comprises one or more active agents and one or more excipients to maintain chemical and physical stability of the active agent(s), and the particle shell is comprised of a layer of a hydrophobic excipient, wherein the hydrophobic excipient aids in reducing interparticle cohesive forces.

Suitable examples of dispersibility-enhancing agents comprise di- or tripeptides containing two or more leucine residues. Suitable are amino acids such as glycine (gly), alanine (ala), valine (val), leucine (leu), isoleucine (ile), methionine (met), proline (pro), phenylalanine (phe), trytophan (trp), serine (ser), threonine (thr), cysteine (cys), tyrosine (tyr), asparagine (asp), glutamic acid (glu), lysine (lys), arginine (arg), histidine (his), norleucine (nor), and modified forms thereof. Particularly preferred peptides are dileucine and trileucine. Also preferred are di- and tripeptides having a glass transition temperature greater than about 40° C. In some embodiments, surface active di- and tripeptides are used.

Glass-forming excipients may be utilized to improve the physical and chemical stability of an amorphous solid. These excipients may also be used as bulking agents in the formulation for highly potent active agents. Suitable glass-forming excipients include carbohydrates (e.g., sugars, derivatized sugars such as alditols, aldonic acids, esterified sugars, and sugar polymers), which may be present singly or in combination. Suitable excipients include those provided in U.S. Pat. No. 6,187,344, which is incorporated herein by reference in its entirety. The excipient may have a glass transition temperature ($T_g$) above about 50° C., often above about 70° C., and even above 100° C. Examples of a suitable glass-forming carbohydrate are trehalose ($T_g$=117.0° C.) and sucrose ($T_g$=73.4° C.).

In order to slow molecular motions in amorphous solids, combinations of sugars with alditols may be utilized. Glass-forming excipients, such as trehalose, form vitreous glasses with active agents, thereby slowing long-range molecular mobility (i.e., so-called "alpha" relaxation). However, local motions (i.e., "islands of mobility") still remain. These local motions are referred to as "beta" or Johari-Goldstein relaxations. Alditols, like mannitol ($T_g$=11.0° C.), sorbitol ($T_g$=−3.0° C.), and glycerol ($T_g$=−93° C.) have low $T_g$ values and will plasticize or reduce the $T_g$ of the formulation (and increase long-range mobility). Alditols can still improve overall chemical stability by antiplasticizing or suppressing local motions. The optimal ratio of the two carbohydrates for a given active agent may be determined empirically without undue experimentation.

Additional glass forming excipients include salts such as sodium citrate dihydrate ($T_g$=170.0° C., pH>7.0), and hydrophobic amino acids and proteins. Example of suitable amino acids include leucine ($T_g$=140° C.), and dipeptides and tripeptides comprising leucine, such as trileucine ($T_g$=70-100° C., depending on pH). Exemplary protein excipients include albumins such as human serum albumin (HSA), recombinant human albumin (rHA), gelatin, casein, hemoglobin, and the like.

In some embodiments of the present invention, the excipients are shell-forming excipients. These are generally hydrophobic in nature with some degree of surface activity. Examples of suitable agents include phospholipids, amino acids, peptides, and fatty acid soaps.

Phospholipids from both natural and synthetic sources may be used in varying amounts. When phospholipids are present, the amount is typically sufficient to provide a porous coating matrix of phospholipids. Generally compatible phospholipids comprise those having a gel to liquid crystal phase transition greater than about 40° C., such as greater than 60° C., or greater than about 80° C. The incorporated phospholipids may be relatively long chain (e.g., $C_{16}$-$C_{22}$) saturated phospholipids. Exemplary phospholipids useful in the disclosed stabilized preparations include, but are not limited to, phosphatidylcholines, such as dipalmitoylphosphatidylcholine (DPPC), distearoylphosphatidylcholine (DSPC), and hydrogenated egg or soy phosphatidylcholines (e.g., E-100-3, S-100-3, available from Lipoid KG, Ludwigshafen, Germany). Natural phospholipids are preferably hydrogenated, with a low iodine value (<10). The phospholipids may optionally be combined with cholesterol to modify the fluidity of the phospholipid acyl chains.

The long-chain phospholipids may optionally be combined with a divalent metal ion (e.g. calcium, magnesium). Such a divalent metal ion acts to decrease headgroup hydration, thereby increasing the phospholipid gel to liquid crystal phase transition, and the wettability of the powders on lung lining fluid. The molar ratio of polyvalent cation to phospholipid may be at least about 0.02:1, such as about 0.05:1 to 1:2. In one or more embodiments, a molar ratio of polyvalent cation:phospholipid is 0.05:1 to 0.5:1. Molar ratios of metal ion to phospholipid in excess of 0.5 may result in free metal ion not bound to the phosphate groups. When the polyvalent metal ion is calcium, it may be in the form of calcium chloride. Although metal ions, such as calcium, are often included with phospholipids, none is required. In some embodiments, Magnesium$^{++}$ salts may be used as they typically have $K_{sp}$ values which are three to four orders of magnitude higher than Calcium$^{++}$ salts.

The hydrophobic excipient may also comprise long chain fatty acid soaps. The alkyl chain length may be 14-22 carbons in length with saturated alkyl chains preferred. The fatty acid soaps may utilize monovalent (e.g., Na$^+$, K$^+$) or divalent counterions (e.g., Ca$^{++}$, Mg$^{++}$). Particularly preferred fatty acid soaps are sodium stearate and magnesium stearate. The solubility of fatty acid soaps may be increased above the Krafft point. Potassium salts of fatty acids generally have the lowest Krafft point temperature and greater aqueous solubility at a given temperature. Calcium salts are expected to have the lowest solubility. The hydrophobic fatty acid soaps provide a wax-like coating on the particles.

The hydrophobic excipient may also comprise hydrophobic amino acids, peptides, or proteins. Particularly preferred are the amino acid leucine, and its oligomers dileucine and trileucine. Proteins, such as, human serum albumin are also contemplated. Trileucine is particularly preferred, as its solubility profile and other physicochemical properties (e.g., surface activity, log P) facilitate creation of core-shell particles, where trileucine controls the surface properties and morphology of the resulting particles. These excipients have high $T_g$ values, and as a result do not negatively impact the amorphous solid present in the core of the particle.

In some embodiments of the present invention the formulation for inhalation may contain additives to further enhance the stability or biocompatibility of the formulation. For example various salts, buffers, surfactants, chelators, bulking agents, common ions, antioxidants, targeting agents, and taste-masking agents are contemplated. The use of these additives will be understood to those of ordinary skill in the art and the specific quantities, ratios, and types of agents can be determined empirically without undue experimentation.

The pharmaceutical formulation may also include polymeric excipients/additives, e.g., polyvinylpyrrolidones, derivatized celluloses such as hydroxymethylcellulose, hydroxyethylcellulose, and hydroxypropylmethylcellulose, Ficolls (a polymeric sugar), hydroxyethylstarch, dextrins (e.g., cyclodextrins, such as 2-hydroxypropyl-β-cyclodextrin and sulfobutylether-β-cyclodextrin), polyethylene glycols, and pectin.

In embodiments of the invention, the formulations for use with the present invention include engineered particle formulations, such as those described in, U.S. Pat. No. 7,306,787; U.S. Pat. No. 7,442,388; U.S. Pat. No. 6,051,256; and U.S. Pat. No. 6,518,239, all of which are incorporated herein by reference in their entireties. These described particles comprising excipients, and/or are made under processes that give the particles a high (greater than about 2) rugosity, high porosity, and/or hydrophobic surfaces that make the particles aerosolizable at relatively low flow rates, such as flow rates desired for the present invention. As discussed above, particularly preferred excipients in these formulations include phospholipids, carbohydrates, amino acids such as leucine and trileucine, and metal ions such as calcium.

In one version, the dry powder particles may have a tapped density less than 0.4 g/cm$^3$, or less than about 0.3 g/cm$^3$, or less than about 0.2 g/cm$^3$ or, less than 0.1 g/cm$^3$. In some embodiments, tapped density will depend upon device features and powder properties. In one version for use with apparatus 100, the dry powder comprises a phospholipid-based porous powder, having a tapped density of less than about 0.05 g/cm$^3$, or of about 0.04 g/cm$^3$.

The engineering of device and/or formulation features enables drug delivery which is largely independent of the subject's inhalation profile. In this regard, it is desirable to achieve powder dispersion where the inertial parameter is constant in the range of flow rates covering pressure drops from 1 kPa to 6 kPa, and any value therebetween, such as between 1 kPa to 5 kPa, or 1 kPa to 4 kPa, or 1 kPa to 3 kPa, or 1 kPa to 2 kPa.

Increasing PIF impacts total lung deposition in two competing ways: (a) it increases inertial impaction in the oropharynx, thereby decreasing lung deposition; and (b) it increases powder dispersion, thereby increasing lung deposition. For spheronized particles (e.g., Pulmicort® Turbuhaler®, Astra-Zeneca), the improvements in powder dispersion achieved with increases in PIF outweigh losses due to inertial impaction, resulting in significant increases in lung deposition with increases in PIF. A similar trend is noted for ordered mixtures with coarse lactose, although the magnitude of the effect is not as large, and can be mitigated to some degree through device design.

Porous particles when used in the present apparatus disperse with little applied energy, and provide a means to balance the two competing effects, leading to flow rate independence in lung deposition over a wide range of PIF.

Also, when treating lung diseases such as asthma and COPD, the aerosolization device should be effective in consistently aerosolizing relatively small receptacle fill masses. For example, in one version the fill masses may range from about 0.3 mg to about 10 mg, more preferably from about 1 mg to about 5 mg. In asthma/COPD treatment, nominal doses are often in the range of from about 5 mcg to about 500 mcg. Accordingly, for these pharmaceutical formulations, the relative portion of excipient in the particles can be very high. This high excipient loading has the added advantage of allowing the surface composition and morphology to be controlled more by the excipient than the active agent.

In one or more embodiments, the present invention comprises a passive inhaler device and a powder for delivering an active agent to a patient or subject. In one or more embodiments a formulation comprises porous particles (PulmoSpherem™ particles), comprising an active agent, a phospholipid excipient, and optionally a multivalent metal ion, such as calcium chloride, the particles having a mass median geometric diameter of about 3.4 µm, and a tapped density of about 0.04 g/cm$^3$. The formulation is administered by a passive inhaler of the present invention, having, in one embodiment, a device resistance of about 0.17 [cm H$_2$O$^{1/2}$/L min$^{-1}$]. The powder properties of high lung delivery efficiency coupled with low inter-patient variability administered with the inhaler device of the present invention can dramatically reduce the impact of differences in inhalation maneuvers on drug delivery, thus improving efficacy and consistency. Studies on asthma/COPD subjects have shown that virtually all subjects could achieve a pressure drop of 1 kPa or more, and an inhaled volume of at least 500 mL. In-vitro measures of 'lung dose' with PulmoSphere™ placebo particles were found to be largely independent of the simulated patient inhalation profiles (flow rate, inhaled volume, and ramp time) across the broad range of inhalation profiles.

In this way powder fluidization and dispersibility are controlled by the surface composition and morphology and not by the nature of the active agent. This is especially useful for embodiments comprising fixed dose combinations of two or more active agents.

In some versions, the present invention thus comprises a device and includes a dry powder having a particle size selected to permit penetration into the lungs, that is, less than 30 µm mass median diameter (MMD), preferably less than 20 µm, more preferably less than 10 µm, and most preferably less than 5 µm, and usually being in the range of 0.1 µm to 5 µm in diameter. The delivered dose efficiency (DDE) of these powders may be greater than 60%, more preferably greater than 70%, more preferably greater than 80%, and most preferably greater than 90%, and the aerosol particle size distribution is about 1.0-5.0 µm mass median aerodynamic diameter (MMAD), usually 1.5-4.5 µm MMAD and preferably 1.5-4.0 µm MMAD. These dry powders may have a moisture content below about 10% by weight, usually below about 5% by weight, and preferably below about 3% by weight.

In one embodiment of the present invention, the device and formulation achieve $\rho d_{ae}^2 Q$=constant, as a function of variations in Q (i.e., flow rate independence) over a range of pressure drops in the device from 1 kPa to 6 kPa. One consequence of the desire to achieve lung delivery which is independent of flow rate is that the aerodynamic particle size distribution must get finer with increases in Q to achieve a constant impaction parameter, $d_{ae} \propto Q^{-1/2}$.

In an embodiment of the present invention, the device and formulation achieve $\rho d_{ae}^2 Q \leq 20,000$ g µm$^2$ s$^{-1}$, or $\leq 10,000$ g µm$^2$ s$^{-1}$. This ensures that mean lung deposition will be greater than about 40% of the delivered dose. In embodiments of the invention, mean lung deposition is greater than, 50% or 55% or 60% or 65% or 70% or 75% or 80% or 85% or 90% or 95%, of the delivered dose. In embodiments of the invention, mean interpatient variability is less than 10-20%, by reducing the variability associated with oropharyngeal filtering, resulting from anatomical differences in the mouth-throat.

The present invention allows for more effective timing of the blister emptying event in relation to the inhalation profile of the patient, i.e., limits the impact of ramp times to peak flow on aerosol performance. The mean ramp time to 60% of peak flow ($t_{60}$) with the present apparatus in asthma and COPD patients is about 180 ms and 190 ms, respectively. Depending on device design features, powder may empty the blister as a bolus with an emptying time of 100 ms or less. By judicious control of air flow through the receptacle and bypass, it is possible to control the onset of powder emptying from the blister, and to extend the time over which the powder emptying event takes place. In one embodiment, it is advantageous to delay the emptying event by at least 50 ms, or by at least 100 ms. It is also desirable to increase the total emptying time to more than 300 ms, or more than 500 ms.

Example 1: Inspiratory Flow Profiles for Asthma/COPD Patients with an Aerosolization Apparatus According to the Invention In order to achieve the desired goal of lung deposition which is independent of the patient's inhalation profile, the inhalation profiles were determined for the target patient population through the apparatus 400 described above. A clinical study was conducted in 72 subjects with asthma and COPD. When asked to breathe forcefully for at least 2 seconds through the apparatus 400 mouthpiece attached to a differential pressure gauge, the mean maximum inspiratory pressure (MIP) values in asthma and COPD subjects were 6.3 kPa and 5.4 kPa, respectively. Approximately 90% of the subjects were able to achieve a MIP of at least 4 kPa, and only 3 of the 72 subjects (two 4 year old asthma patients and a 79 year old COPD patient) failed to achieve a MIP of at least 2.4. Literature suggests that breathing comfortably occurs at about 0.55 MIP for a wide range of subjects, including healthy volunteers and patients with lung disease. Based on these results, the average asthma/COPD patient should be able to comfortably pull 3.0 to 3.5 kPa (e.g., 0.55×6.3 kPa), while those on the bottom of the curve should be able to pull at least 1.3 kPa through device 400.

Inhalation profiles were also measured through a device 400 simulator comprising a mouthpiece, resistance, and flowmeter. More than 95% of the patients (n=72) achieved a pressure drop of at least 1 kPa and an inhaled volume of greater than 0.5 L. The 1 kPa and 0.5 L values have been selected as our lower limit targets for in-vitro aerosol testing over which the measured fine particle dose or "lung dose" must be equivalent to the standard in-vitro aerosol test condition (ΔP~4 kPa, $V_i$~2,000 mL). For purposes herein equivalence is defined as being within ±15% of the value at a 4 kPa pressure drop.

Example 2: Preparation of Engineered Powders

Placebo PulmoSphere™ powders (Novartis Pharmaceutical Corporation, San Carlos, Calif.) were manufactured by spray-drying a feedstock comprising an oil-in-water emulsion on a Niro PSD-1 scale spray-drier equipped with custom atomization and collection hardware. The porous particles exhibit the sponge-like morphology characteristic of the PulmoSphere process. The particles are comprised of a 2:1 molar ratio of distearoylphosphatidylcholine to calcium chloride. The size of the particles and their tapped density is controlled by the atomization conditions, drying rate, feedstock solids content, and volume fraction of oil in the emulsion. The oil phase is comprised of perfluorooctyl bromide.

TABLE 1

PHYSICOCHEMICAL PROPERTIES OF ENGINEERED PARTICLE FORMULATIONS

| Lot # | Active agent | x50 (µm) | Tapped density(g/cm$^3$) |
|---|---|---|---|
| 700 | None | 2.5 | 0.04 |
| 710 | None | 3.5 | 0.04 |
| 720 | None | 4.2 | 0.04 |
| 730 | None | 2.0 | 0.07 |
| 740 | None | 3.2 | 0.07 |
| 750 | None | 1.7 | 0.12 |

Primary particle size distributions were determined by laser diffraction. Powder samples were measured using a Sympatec Oasis instrument comprising a HELOS unit (with an R2 lens) equipped with a RODOS/M dry powder dispersing unit (Sympatec GmbH, Clausthal-Zellerfeld, Germany). Samples were filled into glass vials and introduced to the instrument via an ASPIROS micro dosing powder feeder. The following settings were applied for analysis of samples: a sample mass of approximately 10 mg, an optical concentration of approximately 1%, and a driving pressure of 4 bar. Data were collected over a period of 10 s. Particle size distributions were calculated from the instrument software using a Fraunhofer model. A total of three replicates were taken per measurement.

Tapped densities were determined by measuring the mass of powder required to fill a cylindrical cavity (a uniaxial compaction, UC cell, of known volume) using a microspatula. The sample holder was gently tapped on the countertop. More powder was added to the cell as the sample volume decreased. The tapping and addition of powder steps were repeated until the cavity was filled and the powder bed no longer consolidated with further tapping.

Example 3: Filling of Spray-Dried Powders into Unit Dose Receptacles

Spray-dried powders were filled into foil-foil blisters with a proprietary volumetric drum filler (Novartis Card Filler, San Carlos, Calif.). Key elements of the filler include a powder feed trough used to produce a uniform, well fluidized powder bed above a rotatable metal drum provided with a row of cylindrical cavities of precise volume. Application of vacuum to the filter lined cavity bottom allows metering of a precise volume of powder into the cavities. The drum is then rotated and pressure applied to eject a compressed powder puck into a row of foil blisters positioned below the drum. A foil lidstock is then heat-sealed onto the blister cavity. The nominal fill mass was 1 mg to 2 mg, and the RSD was less than 4%. Filled blisters were conditioned with a pulse of ultrasonic energy to re-disperse the pucks.

Example 4: Impact of Powder Properties on Powder Emptying from the Receptacle

FIG. 15 shows percent blister retention as a function of flow rate through the blister for six different PulmoSphere placebo formulations (700-750). Significant differences in powder fluidization are observed both as a function of variations in primary particle size, tapped density, and flow rate through the blister. For $Q_B$=1-10 L min$^{-1}$, significant increases in blister retention are observed when x50<2.5 microns, or when the tapped density is greater than 0.04 g/cm$^3$. Only small effects are noted with primary particle size for 2.55≤x50≤4.2 microns. Significant powder retention in the blister and accentuation in the differences between powder formulations is observed for $Q_B$<1 Lmin$^{-1}$. It can be concluded from these results that higher density powders (e.g., micronized drug blends or spheronized particles) would be expected to have poor powder emptying from the blister in aerosolization apparatus 100. Hence, lower density engineered particles which can be effectively fluidized and dispersed at flow rates less than 10 L min$^{-1}$ are preferred.

Emitted powder masses (EPM) from a passive blister inhaler device in accordance with embodiments of the present invention (e.g. inhaler 400) were determined gravimetrically. The EPM data were collected at a pressure drop of 4 kPa, corresponding to a flow rate of about 35 L min$^{-1}$. The volume of air sampled was 2 L. The powder emitted from the inhaler was collected on a filter (Pall Life Sciences P/N 61631), and its mass determined using a microbalance.

Example 5: Flow Rate Independence of Engineered Particles in Device 400

Figure 16:
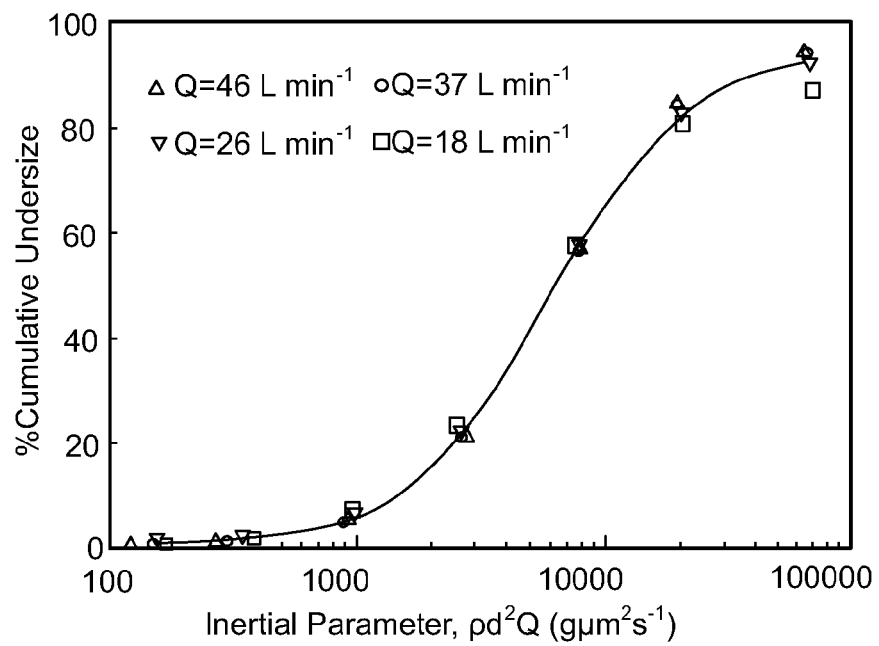
FIG. 16 is a plot of the cumulative mass distribution of a PulmoSphere™ placebo powder delivered with an apparatus of the invention as a function of the inertial parameter for various test flow rates.

The emitted powder mass and aerodynamic particle size distributions of a PulmoSphere placebo powder (Lot 7) administered with device 400 were assessed on a Next Generation Impactor, (as shown in Table 2 and FIGS. 15 and 16). Table 2 presents various in-vitro measures of aerosol performance including the emitted powder mass (EPM), mass median aerodynamic diameter (MMAD), and the fine particle mass (FPM) for stage groupings S3-F, and S4-F. Also presented is the inertial parameter, $\rho d^2 Q$, where $\rho$ is the particle mass density, d is the aerodynamic diameter, and Q is the flow rate. This single parameter captures the combined effect of flow rate and particle size on inertial impaction in the mouth-throat. The data is presented as a function of variations in flow rate from 18 L min$^{-1}$ to 46 L min$^{-1}$, corresponding to pressure drops in the Inhaler of 1, 2, 4, and 6 kPa. The EPM increases from 80% at 18 L min-1 to 86% at 46 L min-1 (1 mg fill mass). This is a reflection of improved powder fluidization and blister emptying at the higher flow rates.

A plot of the cumulative aerodynamic particle size distributions for the various flow rates tested is presented in FIG. 16 (2 mg fill mass). The distributions are plotted not as a function of aerodynamic diameter, but instead as a function of variations in the inertial parameter, $\rho d_{ae}^2 Q$. This provides a better reflection of the impact of variations in flow rate on inertial impaction in the URT. This is essentially a plot of the cumulative distribution of powder on the various impactor stages, where the highest value of the inertial parameter corresponds to deposition on Stage 1. The little variation observed in the cumulative distributions reflects that inertial impaction on the various stages of the impactor is independent of flow rate.

This is further demonstrated in the lack of statistically significant differences in powder deposition for the 'respirable' stage groupings (e.g., S3-F, S4-F). The mean FPMS4-F at a standard pressure drop of 4 kPa (0=37 L min-1) was 46.1% of the nominal dose. At 6 kPa (Q=46 L min-1), the mean FPMS4-F was 45.3%, or 1.7% less than the value obtained at 4 kPa. Similarly, at a pressure drop of 2 kPa (Q=26 L min-1), the mean FPMS4-F was 45.2%, or 2.0% less than the value at 4 kPa. Even at a pressure drop of just 1 kPa (Q=18 L min-1), a FPMS4-F of 42.7% was obtained. This corresponds to a decrease of 7.4% relative to this measurement at 4 kPa. Within the context of a Tukey-Kramer one-way ANOVA analysis, there is statistically no difference between any of the pressure drops tested. Similar results are obtained for FPMS3-F.

Figure 17:
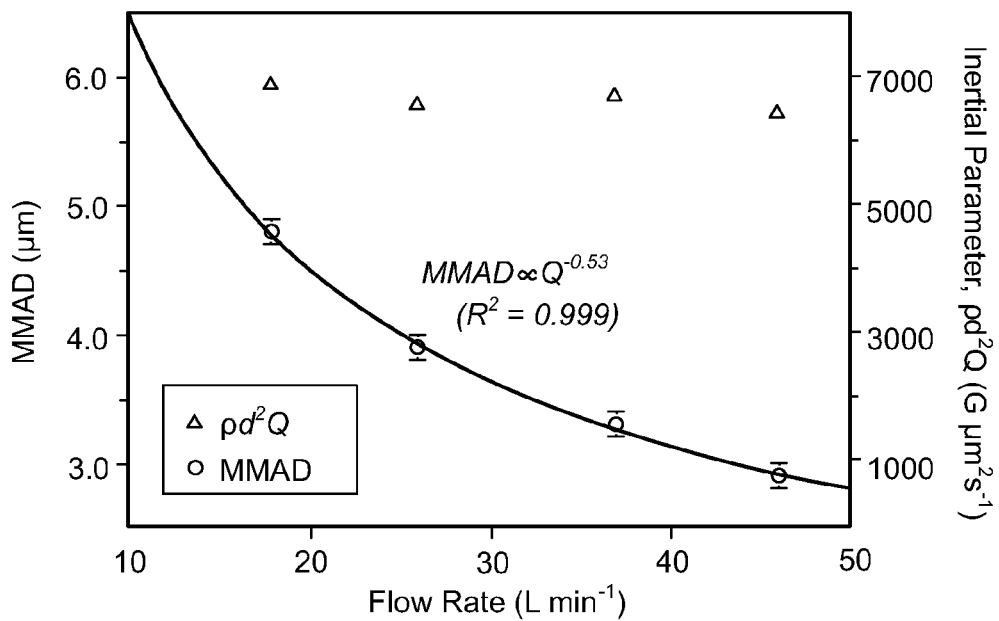
FIG. 17 is a plot of the mass median aerodynamic diameter (MMAD) and inertial parameter ($\rho d_{ae}^2 Q$) for PulmoSphere™ placebo particles delivered with an apparatus of the invention as a function of flow rate where each MMAD value represents the mean of three replicates with the error bars representing the standard deviation.

In one or more embodiments lung delivery which is independent of flow rate may be achieved by adjusting the aerodynamic particle size distribution (e.g. MMAD) in conjunction with the Q parameter. Thus, the aerodynamic particle size distribution becomes finer with increases in Q. FIG. 17 presents a plot of the MMAD versus Q. MMAD values increased from 2.9 μm at 46 L min-1 to 4.8 μm at 18 L min-1. An excellent fit is observed for MMAD∝$Q^{-0.5}$. Hence, the dependence of MMAD with Q effectively compensates for the increases in URT impaction anticipated at higher flow rates.

Also presented in FIG. 17 is a plot of the inertial parameter, $\rho d_{ae}^2 Q$ as a function of flow rate. The inertial parameter is calculated for $d_{ae}$=MMAD. The values of $\rho d_{ae}^2 Q$ obtained are independent of flow rate, consistent with the cumulative distributions shown in FIG. 16.

The impact of variations in flow rate was further assessed using the idealized Alberta URT model (Table 3). The idealized Alberta cast was designed to provide a model for average URT deposition of inhaled aerosols. Determination of the idealized Alberta cast was based on a series of deposition studies with realistic URT geometries obtained from magnetic resonance imaging. Deposition of Pulmo-Sphere placebo particles in the URT was low (ca., 13-15% of the nominal dose) and consistent across a range of pressure drops from 16 L min-1 to 40 L min-1 (Table 3). Most of the observed difference in 'lung dose' (i.e., deposition on the filter post-URT) is the result of the small decreases in EPM observed with decreases in flow rate. The magnitude of the difference in 'lung dose' at 1 kPa and 6 kPa from the 4 kPa baseline is 6.7%. This is considered to be an equivalent result.

Figure 18:
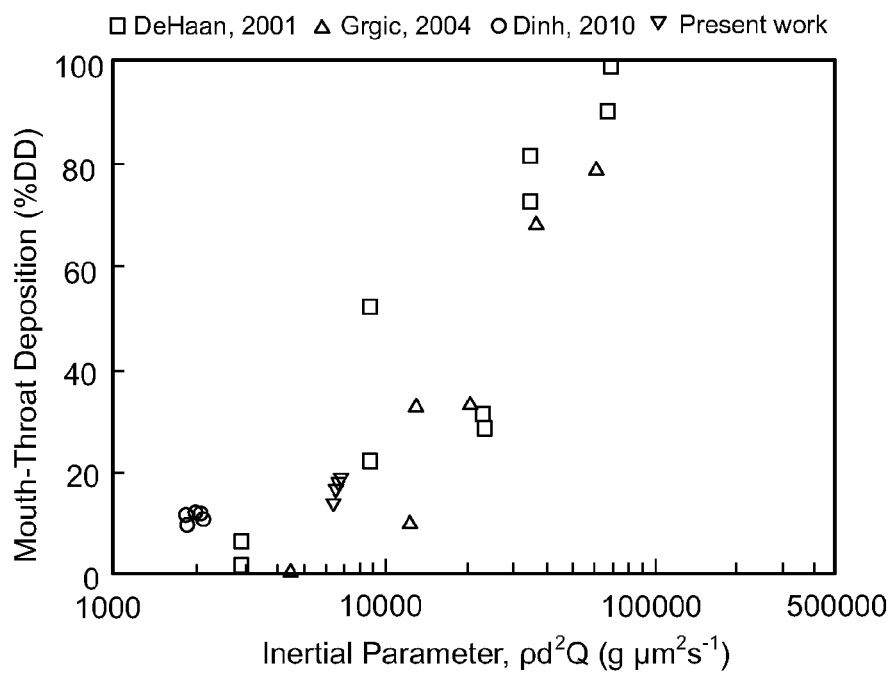
FIG. 18 is a plot of upper respiratory tract deposition as a function of the inertial parameter in the idealized Alberta URT model (data from Table 3 herein) and includes points from previous using the Alberta cast.

The magnitude of URT deposition observed for the values of $\rho d_{ae}^2 Q$ achieved with the PulmoSphere placebo particles is consistent with previous studies of mouth-throat deposition using the idealized Alberta URT (FIG. 18). The clustering of the points at various flow rates is indicative of the consistency in the inertial impaction parameter with variations in Q. The 'lung dose' from the idealized Alberta cast is high (i.e., 70-80% of the nominal dose).

The in-vitro results presented for PulmoSphere placebo particles in the device 400 are consistent with lung deposition which is independent of flow rate over pressure drops from 1 kPa to 6 kPa. This encompasses more than 90% of asthma/COPD patients. This was achieved by adjustment of powder properties and device 400 receptacle outflow diameter and receptacle and bypass flow.

TABLE 2

IN-VITRO AEROSOL PERFORMANCE IN A NEXT GENERATION IMPACTOR AS A FUNCTION OF FLOW RATE OR PRESSURE DROP ACROSS THE DEVICE 400

| ΔP [kPa] | Q [L min$^{-1}$] | EPM [% Nominal] | N | MMAD [μm] | FPM$_{S3-F}$ [% Nominal] | FPM$_{S4-F}$ [% Nominal] | $\rho d_{ae}^2 Q$ [g μm$^2$ s$^{-1}$] |
|---|---|---|---|---|---|---|---|
| 1 | 18 | 80 ± 4 | 3 | 4.8 ± 0.1 | 60 ± 4 | 42 ± 1 | 6,926 |
| 2 | 26 | 81 ± 4 | 6 | 3.9 ± 0.1 | 65 ± 2 | 45 ± 2 | 6,604 |
| 4 | 37 | 81 ± 6 | 15 | 3.3 ± 0.1 | 69 ± 3 | 46 ± 2 | 6,729 |
| 6 | 46 | 86 ± 3 | 6 | 2.9 ± 0.1 | 68 ± 4 | 45 ± 4 | 6,461 |

EPM testing was conducted with a 1 mg fill mass; APSD testing was conducted with a 2 mg fill mass The impaction parameter was calculated using the MMAD as the diameter; the mass density is assumed to be equal to 1.0 g cm$^{-3}$ The mean resistance of the device 400 inhalers utilized was: 0.17 cm H$_2$O$^{1/2}$ LPM$^{-1}$ The Alberta cast was fabricated from Accura® 60 plastic by a stereolithography process. A 47 mm customized filter holder (Thermo Scientific Nalgene Polysulfone Holder) was placed downstream of the Alberta cast, for in-vitro determination of the "lung dose". A polysorbate wetting agent (EMD Chemicals Cat #8170072) comprising equal parts Tween 20 and methanol was used for coating the interior wall of the Alberta cast.

TABLE 3

IN-VITRO LUNG DOSE OBTAINED IN THE IDEALIZED ALBERTA URT MODEL AS A FUNCTION OF FLOW RATE

| ΔP [kPa] | Q [L min$^{-1}$] | EPM [% Nominal] | URT Deposition [% Nominal] | Lung Dose [% Nominal] |
|---|---|---|---|---|
| 1 | 16 | 85 ± 3 | 15 ± 4 | 70 ± 4 |
| 2 | 22 | 88 ± 2 | 13 ± 1 | 74 ± 1 |
| 4 | 32 | 90 ± 2 | 15 ± 5 | 75 ± 5 |
| 6 | 40 | 92 ± 2 | 13 ± 6 | 80 ± 6 |

EPM testing was conducted with a 2 mg fill mass; APSD testing was conducted with a 2 mg fill mass
The mean resistance of the device 400 inhalers utilized was: 0.20 cm H$_2$O$^{1/2}$ LPM$^{-1}$ Example 6: Impact of Ramp Rate on Aerosol Performance For apparatus 400, powder emptying is controlled by the blister package receptacle outlet hole diameter and air flow rate through the receptacle. A 1.2 mm receptacle hole is comparable to the hole punched in hypromellose capsules in the marketed TOBI® Podhaler® device (Novartis Pharmaceuticals Corporation, San Carlos, Calif.). The absence of significant ramp rate effects on in-vitro aerosol performance is illustrated in Table 4. The "slow" ramp rate, expressed as the time to achieve 60% of the PIF was about 18-25% slower than the mean ramp rates observed in asthma/COPD patients, while the "fast" ramp was 42-45% faster than the mean ramp rates. No significant differences in EPM, MMAD, FPM$_{S3-F}$, FPM$_{S4-F}$ or $d_{ae}^2 Q$ were observed for the slow and fast ramp rates.

TABLE 4

IN-VITRO AEROSOL PERFORMANCE IN A NEXT GENERATION IMPACTOR AS A FUNCTION OF RAMP TIME TO PEAK FLOW WITH THE DEVICE 400 INHALER

| t$_{60}$ [ms] | N | Q [L min$^{-1}$] | EPM [% Nominal] | MMAD [μm] | FPM$_{S3-F}$ [% Nominal] | FPM$_{S4-F}$ [% Nominal] | $\rho d_{ae}^2 Q$ [g μm$^2$ s$^{-1}$] |
|---|---|---|---|---|---|---|---|
| 105 | 15 | 37 | 81 ± 6 | 3.3 ± 0.1 | 69 ± 3 | 46 ± 2 | 6729 |
| 225 | 6 | 37 | 83 ± 5 | 3.2 ± 0.1 | 68 ± 3 | 47 ± 3 | 6327 |

EPM testing was conducted with a 1 mg fill mass; APSD testing was conducted with a 2 mg fill mass The impaction parameter was calculated using the MMAD as the diameter; the particle density is assumed to be equal to 1.0 g cm$^{-3}$ The mean resistance of the device 400 inhalers utilized was: 0.17 cm H$_2$O$^{1/2}$ LPM$^{-1}$

Example 7: Inhaled Volume

Figure 19:
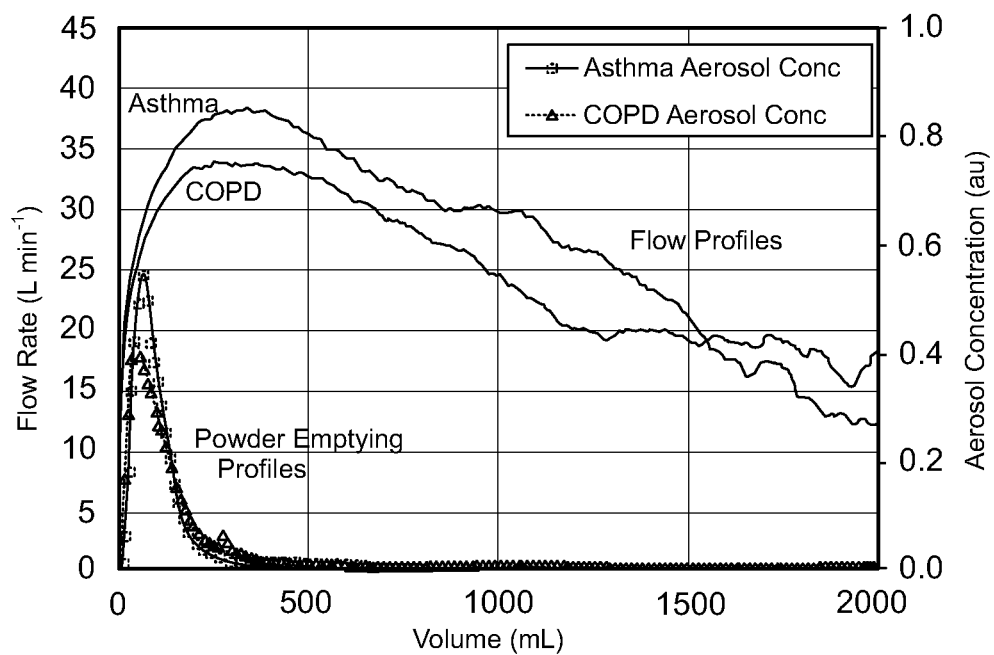
FIG. 19 is a plot of the average flow profiles for asthma and COPD patients through an apparatus of the invention; also shown are the powder emptying profiles obtained for these flow profiles by laser photometry.

The average flow profiles for asthma and COPD patients through the Device 400 Inhaler simulator are presented in FIG. 19. The mean PIF values were 38 L min-1 and 34 L min-1 for the asthma and COPD patients, respectively. This corresponds to a pressure drop of about 4 kPa. The mean inhaled volumes extended beyond 2.0 L. The mean $t_{60}$ values for the asthma and COPD patients were 180 ms and 190 ms, respectively.

To assess the impact of variation in inhaled volume on dose inhalation errors, one must assess the timeframe for powder emptying from the device. This is accomplished using laser photometry. In this experiment, a target breathing profile is simulated and powder emptying from the device is assessed by measuring changes in optical density of the aerosol using a laser beam situated in the flow path. The emptying profiles for PulmoSphere placebo powders from Device 400 are presented in the context of the average inhalation profiles determined in the breathing studies in FIG. 19. Powder emptying occurs very early in the patient's inhalation, extending to an inhaled volume of about 350 mL. Assuming that an additional 150 mL of inhaled volume is required to push the aerosol past the oropharynx and into the conducting airways, then only about 500 mL of inhaled volume is required to effectively deliver the contents of the blister to the lungs. As discussed previously, virtually all asthma/COPD patients can achieve an inhaled volume of at least 0.5 L. Hence, it is unlikely that differences in inhaled volume between patients will have a significant impact on pulmonary drug delivery with apparatus 400.

The emptying profile for powder emission from the blister was assessed by laser photometry. The laser photometer generates a laser light sheet that intersects the flow path of the emitted aerosol immediately downstream of the inhaler mouthpiece. The obscuration of the laser sheet caused by the emitted aerosol bolus is detected by a photodetector. The photodetector's response is linear with obscuration, and Beer's law is used to convert the response into an aerosol concentration. The signal intensity due to aerosol emission is observed as a voltage pulse whose width corresponds to the duration of the aerosol emission process.

Example 8: Variability Associated with Filtering of Particles in the URT

An important factor controlling in-vivo variability during oral inhalation are biological differences in the anatomy of the URT. Lung deposition data from 71 gamma scintigraphy studies had been retrospectively analyzed by Borgström and Olsson, and revealed significant reductions in interpatient variability when total lung deposition exceeded 40% of the delivered dose. The mean lung deposition for currently marketed asthma/COPD dry powder inhalers comprising micronized drug is typically in the range from 10-30%. This results in mean RSD values in lung deposition of 30% to 50%. In contrast, porous particles delivered from capsule-based inhalers exhibit RSDs of just 10-20% (40-70% lung deposition).

Figure 20:
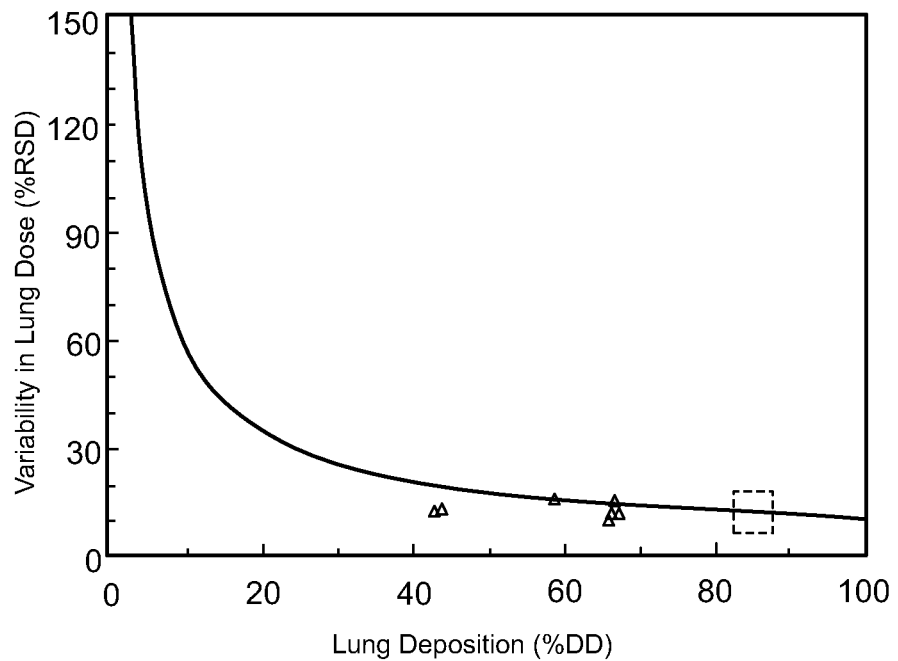
FIG. 20 is a plot of the variability in lung dose as a function total lung deposition.

FIG. 20 plots the variability in the lung dose as a function of total lung deposition. The line represents the fit to the Borgström data. The triangles represent in-vivo gamma scintigraphy results for porous particle formulations delivered with capsule-based devices in healthy volunteers. The mean variability for the seven studies is just 12%. Finally, the box represents the range of lung deposition data obtained from the idealized Alberta mouth-throat from Table 2. Using the fit to the Borgström/Olsson data, in some embodiments the Device 400 and PulmoSphere powder formulation combination will have in-vivo variability in lung deposition of about 8-15%, such as 9-13% or 10-12%.

Example 9: Simulated Inhalation Profiles of COPD Patients

Testing was conducted with the Alberta cast model for a range of simulated inhalation profiles (Table 5). Simulated patient inhalation profiles were generated using a custom breath simulator system. The breath simulator is equipped with a computer-controlled proportional solenoid valve. When the system is connected to a vacuum source, the valve opening can be carried out in a controlled manner to play back a patient flow rate profile selected from a library of flow profiles. The individual profiles were from subjects in the breathing study (Example 1), and were selected to cover the range of profiles anticipated for COPD patients, and extend from about, 1 kPa to 6 kPa. The inhalation profile for the patient with a pressure drop of about 1 kPa, also has a small inhaled volume (<0.5 L) and a very long ramp time ($t_{60}$=510 ms). As such, this profile represents a worst case scenario for all of the critical features encompassing the inhalation profile. Nonetheless, the mean filter deposition (post-URT) in the idealized Alberta URT model remained high (>60% of the nominal dose), falling about 13.0% from the selected 4 kPa profile.

TABLE 5

IN-VITRO LUNG DOSE OBTAINED IN THE IDEALIZED ALBERTA MOUTH-THROAT MODEL WITH SIMULATED INSPIRATORY FLOW PROFILES FROM A RANGE OF COPD PATIENTS

| Age | ΔP [kPa] | PIF [L $min^{-1}$] | Vi [mL] | $t_{60}$ [ms] | Lung Dose [% Nominal] |
|---|---|---|---|---|---|
| 72 | 1 | 18 | 481 | 510 | 60 ± 10 |
| 72 | 2 | 26 | 1487 | 240 | 62 ± 12 |
| 80 | 4 | 36 | 1094 | 110 | 69 ± 1 |
| 70 | 6 | 45 | 1732 | 80 | 73 ± 2 |

Each value of the lung dose is an average of three runs ± 1 SD
Lung dose represents the dose which is deposited on the filter Taken together these data provide confidence that the porous particle/device device combination of the present invention can achieve lung delivery which is largely independent of the inhalation profiles of asthma/COPD subjects. In some embodiments, a flow rate target may be $MMAD \propto Q^{0.5}$, or $MMAD \propto Q^{0.69}$ (accounting for turbulence in the mouth-throat).

In one or more embodiments, the dependence of powder dispersion of porous particles with variations in Q can be adjusted in the porous particle/inhaler device combination of the present invention via adjustment of device features (e.g., blister hole diameter, flow rate through the blister, flow rate through the bypass, device resistance), together with optimization of powder properties (e.g., geometric size, density, porosity). For example, FIG. 15 shows the impact of variations in density of porous particles on emptying from the blister. Increasing the density of the powder results in increases in interparticle cohesive forces leading to increases in blister retention due to decreased powder fluidization (i.e., the lift forces generated in the inhaler are no longer large enough to fluidize the powder). This will also impact the relationship of powder dispersion with Q, as powder dispersion is also impacted by lift and drag forces in the inhaler.

For formulations comprising corrugated particles, the degree of surface roughness or asperities is of importance in modifying interparticle cohesive forces and the resultant powder fluidization and dispersibility. The drag and lift forces may also be manipulated by varying features of the device (e.g., flow rate through blister, blister hole diameter, ratio of bypass air to blister flow, FIG. 13). The adjustment of the drug/device combination to achieve a targeted relationship between the aerodynamic diameter and flow rate may be determined empirically, but one which can be arrived at without undue experimentation by one of ordinary skill using the teachings and analytical methods (e.g., URT deposition) provided herein.

Although the present invention has been described in considerable detail with regard to certain preferred versions thereof, other versions are possible, and alterations, permutations and equivalents of the version shown will become apparent to those skilled in the art upon a reading of the specification and study of the drawings. For example, the cooperating components may be reversed or provided in additional or fewer number. Also, the various features of the versions herein can be combined in various ways to provide additional versions of the present invention. Furthermore, certain terminology has been used for the purposes of descriptive clarity, and not to limit the present invention. Therefore, any appended claims should not be limited to the description of the preferred versions contained herein and should include all such alterations, permutations, and equivalents as fall within the true spirit and scope of the present invention.

What is claimed is:

1. A powder aerosolization apparatus comprising:
   a housing comprising an outlet adapted to be inserted into a user's mouth and one or more bypass air openings,
   a receptacle support within the housing capable of supporting a receptacle containing a powder pharmaceutical formulation,
   a conduit in communication with the outlet and adapted to transport aerosolized powder from the receptacle to the outlet, and
   a puncturing mechanism within the housing to create in the receptacle one or more inlet openings and one or more powder outflow openings, wherein the powder outflow openings have a total area of from 0.2 mm$^2$ to 4.0 mm$^2$,
   wherein the outlet is in fluid communication with the one or more powder outflow openings and with the one or more bypass air openings so that upon a user's inhalation through the outlet, air flows through the one or more bypass air openings and through the receptacle to aerosolize the powder pharmaceutical formulation in the receptacle, wherein a ratio of airflow through the one or more powder outflow openings to the airflow through the one or more bypass openings at peak inhalation is from 1:10 to 1:40.

2. The apparatus according to claim 1 wherein a relative flow resistance between the flow through the one or more bypass openings and the one or more powder outflow openings is selected so that flow of aerosolized pharmaceutical formulation through the one or more powder outflow openings does not occur until a predetermined inhalation flow rate is achieved.

3. The apparatus according to claim 2 wherein the predetermined inhalation flow rate is at least 50% of the peak inspiratory flow rate during inhalation.

4. The apparatus according to claim 1 wherein the one or more powder outflow openings are from 0.2 mm$^2$ to 3.2 mm$^2$ in total area.

5. The apparatus according to claim 1 wherein the one or more powder outflow openings are from about 0.5 mm$^2$ to about 0.8 mm$^2$ in total area and wherein the ratio of airflow through the one or more powder outflow openings to the airflow through the one or more bypass openings is from 1:20 to 1:30.

6. The apparatus according to claim 1 further comprising the receptacle and wherein the receptacle is a multi-layered blister package that is insertable into the housing.

7. The apparatus according to claim 1 wherein the housing comprises multiple receptacles and wherein each receptacle may be moved onto the receptacle support into a position where it is in air flow communication with the outlet.

8. The apparatus according to claim 1 wherein a fine particle fraction of an aerosolized dose of powder is greater than about 40%.

9. The apparatus according to claim 1 wherein the puncturing mechanism is adapted to cut or tear one or more arc-shaped inlet openings in the receptacle.

10. A method of aerosolizing a dry powder pharmaceutical formulation, the method comprising:
    providing a housing comprising an outlet in flow communication with one or more bypass openings, the outlet also being in flow communication with a receptacle, the receptacle containing an aerosolizable powder pharmaceutical formulation;
    drawing air through the outlet to cause air to flow through the one or more bypass openings and through one or more inlets in the receptacle and out one or more powder outflow openings in the receptacle thereby aerosolizing the pharmaceutical formulation within the receptacle, wherein the one or more powder outflow openings have a total area of from 0.2 mm$^2$ to 4.0 mm$^2$, and
    wherein a ratio of airflow through the one or more powder outflow openings to the airflow through the one or more bypass openings is from 1:10 to 1:40.

11. The method according to claim 10 wherein the flow of aerosolized pharmaceutical formulation through the one or more powder outflow openings does not occur until a predetermined inhalation flow rate is achieved.

12. The method according to claim 11 wherein the predetermined inhalation flow rate is at least 50% of the peak inspiratory flow rate during inhalation.

13. The method according to claim 10 wherein the step of drawing air through the outlet comprises having a user inhale though the outlet.

14. The powder aerosolization apparatus of claim 1, further comprising:
    aerosolizable powder pharmaceutical formulation for pulmonary delivery, the powder characterized by an inertial parameter of less than about 20,000 g μm$^2$ s$^{-1}$;
    wherein a delivery of the powder formulation is independent of the user's inhalation profile across a pressure drop of from 1 kPa to 6 kPa, at an inhaled volume of at least 500 mL and with ramp times to 50% of peak inspiratory flow of less than about 190 milliseconds.

15. The powder aerosolization system according to claim 14 wherein the powder pharmaceutical formulation comprises a phospholipid, a divalent metal ion, and an active agent, and wherein the powder is characterized by a tapped density of less than about 0.4 g/cm$^3$, a mass median diameter of from about 1 to about 30 microns, and a mass median aerodynamic diameter of about 1 to 5 microns.

16. The powder aerosolization system according to claim 14 wherein the powder pharmaceutical formulation comprises particulates comprising a core of an active agent, surrounded by a shell of a dispersibility-enhancing excipient, the powder characterized by a mass median diameter of less than 10 microns, and a mass median aerodynamic diameter of about 0.1 to 5 microns.

17. A powder aerosolization system according to claim 14 wherein the powder pharmaceutical formulation comprises a hydrophobic amino acid.

* * * * *